(12) United States Patent
Shattuck et al.

(10) Patent No.: US 7,544,475 B2
(45) Date of Patent: Jun. 9, 2009

(54) DEPRESSION GENE

(75) Inventors: Donna Shattuck, Salt Lake City, UT (US); Deanna Russell, Salt Lake City, UT (US); Victor Abkevich, Salt Lake City, UT (US); Chris Neff, Salt Lake City, UT (US); Lisa Cannon-Albright, Salt Lake City, UT (US); Nicola Camp, Salt Lake City, UT (US)

(73) Assignee: IHC Health Services, Inc. UT (US)

( * ) Notice: Subject to any disclaimer, the term of this patent is extended or adjusted under 35 U.S.C. 154(b) by 3 days.

(21) Appl. No.: 11/750,019

(22) Filed: May 17, 2007
(Under 37 CFR 1.47)

(65) Prior Publication Data

US 2008/0160519 A1    Jul. 3, 2008

Related U.S. Application Data

(60) Continuation of application No. 11/441,887, filed on May 26, 2006, now Pat. No. 7,410,944, which is a division of application No. 10/646,396, filed on Aug. 21, 2003, now Pat. No. 7,052,853.

(60) Provisional application No. 60/405,334, filed on Aug. 21, 2002, provisional application No. 60/428,513, filed on Nov. 21, 2002, provisional application No. 60/442,492, filed on Jan. 24, 2003.

(51) Int. Cl.
*C12Q 1/68* (2006.01)

(52) U.S. Cl. .......................................... 435/6; 536/23.1
(58) Field of Classification Search ............ 435/6; 536/23.1
See application file for complete search history.

(56) References Cited

U.S. PATENT DOCUMENTS 6,291,643 B1    9/2001    Zou et al.
6,346,607 B1    2/2002    Wang

FOREIGN PATENT DOCUMENTS

WO    WO 02/057790    7/2002

OTHER PUBLICATIONS

Acehan, Devrim, et al., "Three- Dimensional Structure of the Apoptosome: Implications for Assembly, Procaspase-9 Binding, and Activation", *Molecular Cell*, Feb. 2002; 9:423432.

Belmokhtar, Chafke Ahmed, et al., "Apoptosome-independent Pathway for Apoptosis", *The Journal of Biological Chemistry*, Aug. 8, 2003: 278(32):29571-29580.
Day et al., 1999; Cell Death and Differentiation 6:1125-1132.
Hu et al., 1999; EMBO 1. 18(13): 3568-3595.
Li, Kang, et al., "Cytochrome c Deficiency Causes Embryonic Lethality and Attenuates Stress-Induced Apoptosis", *Cell*, May 12, 2000; 101:389-399.
Li, Peng, et al., "Cytochrome c and dATP-Dependent Formation of Apaf-1/Caspase-9 Complex Initiates an Apoptotic Protease Cascade", *Cell*, Nov. 14, 1997; 91:479-489.
Nestler, Eric J., et al., "Neurobiology of Depression", *Neuron*, Mar. 28, 2002; 34:13-25.
Nguyen, Jack T., "Direct activation ofthe apoptosis machinery as a mechanism to target cancer cells", *PNAS*, Jun. 24, 2003: 100(13):7533-7538.
Qin et al., 1999; Nature 399:549-557.
Santarelli, Luca, et al., "Requirement of Hippocampal Ncurogenesis for the Behavioral Effects of Antidepressants", *Science*, Aug. 8, 2003; 301:805-809.
Shiozaki, Eric N., et al., "Oligomerization and activation of caspase-9, induced by Apaf-1 CARD", *PNAS*, Apr. 2, 2002; 99(7):4197-4202.
Vaux, David L. et al., "CED-4- The Third Horseman of Apoptosis", *Cell*, Aug. 8, 1997; 90:389-390.
Walke et al., 2000; Brain Res. 886: 73-81.
Yakovlev et al, Oct. 2001; 1. Neuroscience 21(19): 7439-7446.
Yoshida, Hiroki, et al., "Apafl Is Required for Mitochondrial Pathways of Apoptosis and Brain Development", *Cell*, Sep. 18, 1998; 94:739-750.
Zou, Hua, et al., "Apaf-1, a Human Protein Homologous to C. *elegans* CED-4, Participates in Cytochrome c-Dependent Activation of Caspase-3", *Cell*, Aug. 8, 1997; 90:405-413.
Zou, Hua, et al., "An APAF-loCytochromc c Multimcric Complex Is a Functional Apoptosome That Activates Procaspase-9", *The Journal of Biological Chemistry*, Apr. 23, 1999; 274(17):11549-11556.

*Primary Examiner*—Karen Cochrane Carlson
(74) *Attorney, Agent, or Firm*—Knobbe Martens Olson & Bear LLP

(57) ABSTRACT

The present invention relates generally to the field of human genetics. Specifically, the present invention relates to methods and materials used to isolate and detect a human depression predisposing gene, specifically the apoptotic protease activating factor 1 (APAF1) gene, some mutant alleles of which cause susceptibility to depression. More specifically, the invention relates to germline mutations in the APAF1 gene and their use in the diagnosis of predisposition to depression. The invention also relates to the prophylaxis and/or therapy of depression associated with a mutation in the APAF1 gene. The invention further relates to the screening of drugs for depression therapy. Finally, the invention relates to the screening of the APAF1 gene for mutations/alterations, which are useful for diagnosing the predisposition to depression.

5 Claims, 3 Drawing Sheets

DEPRESSION GENE

CROSS-REFERENCE TO RELATED APPLICATIONS

This application is a continuation of U.S. patent application No. 11/441,887 filed on May 26, 2006, now U.S. Pat. No. 7,410,944, which claims priority to U.S. patent application No. 10/646,396 filed on Aug. 22, 2003, now U.S. Pat. No. 7,052,853, which claims priority to U.S. Provisional Application Ser. Nos. 60/405,334, filed on Aug. 21, 2002; 60/428,513, filed Nov. 21, 2002; and 60/442,492, filed Jan. 24, 2003, the contents of which are incorporated herein by reference in their entireties.

SEQUENCE LISTING

The present application is being filed along with a Sequence Listing in electronic format. The Sequence Listing is provided as a file entitled IHCINC__003C1C1_SEQ.txt, created May 15, 2007, which is 18.5 Kb in size. The information in the electronic format of the Sequence Listing is incorporated herein by reference in its entirety.

BACKGROUND OF THE INVENTION

1. Field of the Invention

The invention relates generally to depression. In particular, the invention relates to a gene associated with depression and altered forms of the gene. The invention provides methods for predicting depression, predicting susceptibility to depression, and screening for drugs capable of treating depression.

2. Description of the Related Art

Depression is thought to affect around twenty million Americans every year. The economic impact of depression is difficult to estimate, but reports indicate that approximately 30 billion dollars was lost directly and indirectly in 1990 as a result of the disease. Depression manifests itself in many different ways including persistent sad mood, loss of interest or pleasure in once enjoyable activities, significant change in appetite or body weight, sleep disorders, physical slowing or agitation, loss of energy, feelings of worthlessness, inappropriate guilt, difficulty thinking, difficulty concentrating, malaise, and recurrent thoughts of death or suicide. The families and friends of depressed individuals are often profoundly affected by the disease.

The present invention relates generally to depression. More specifically, the present invention relates to methods and materials used to isolate and detect a human depression predisposing gene, specifically the apoptotic protease activating factor 1 (APAF1) gene, some mutant alleles of which cause susceptibility to depression. More specifically, the invention relates to germline mutations in the APAF1 gene and their use in the diagnosis of predisposition to depression. The invention also relates to the prophylaxis and/or therapy of depression associated with a mutation in the APAF1 gene. The invention further relates to the screening of drugs for depression therapy. Finally, the invention relates to the screening of the APAF1 gene for mutations/alterations, which are useful for diagnosing the predisposition to depression.

Depression is typically diagnosed as major depressive disorder (unipolar major depression, bipolar disorder (manic-depressive illness), and dysthymic disorder (dysthymia). There are a number of subtypes of these major categories of depression. Diagnosis of these mental disorders is based on the Diagnostic and Statistical Manual of Mental Disorders, fourth edition (DSM-IV). American Psychiatric Association; Diagnostic and Statistical Manual of Mental Disorders, fourth edition (DSM-IV), Washington, D.C., American Psychiatric Press, 1994.

Major depression is associated with low mood, low energy and motivation, insomnia, and feelings of worthlessness and hopelessness. Bipolar disorder is a severe psychiatric disorder that affects approximately 1% of the world's population (Goodwin, F. K. and Jameson, K. R. (1990) Manic-Depressive Illness, Oxford Univ. Press, New York). It is characterized by extreme swings in mood between mania and depression. Mania is accompanied by euphoria, grandiosity, increased energy, decreased need for sleep, rapid speech, and risk taking. Psychosis can occur in either state, and there is a 17% lifetime risk for suicide. Dysthymic disorder is considered a milder form of depression with symptom similar to that of major depression.

The etiology of depression is currently unknown, but epidemiological studies argue for a strong genetic component. Family studies indicate an approximately 7-fold increase in risk to first-degree family members (Tsuang, M. T. and Faraone, S. V. (1990) The Genetics of Mood Disorders, Johns Hopkins Univ. Press, Baltimore). Twin studies find an average 4-fold increase in risk to monozygotic vs. dizygotic twins. The mode of genetic transmission is unclear. Although some studies have supported the presence of autosomal dominant major loci (Spence, M. A. et al. (1995) Am. J. Med. Genet. 60:370 376; Rice, J. et al (1987) Arch. Gen. Psychiatry 44:441 447), it has also been argued that bipolar disorder is oligogenic with multiple loci of modest effect.

Although initial attempts at linkage studies met with inconsistent replication (Egeland, J. A. et al. (1987) Nature 325:783 787; Kelsoe, J. R. et al. (1989) Nature 342:238 243; Baron, M. et al. (1987) Nature 326:289 292; Baron, M. (1991) Soc. Biol. 38:179 188), more recently, the accumulation of multiple studies of larger family sets has led to the reproducible identification of several genetic loci associated with depression. These include 4p, 12q, 13q, 18, 21q, and Xq among others (Blackwood, D. H. et al. (1996) Nat. Genet. 12:427 430; Dawson, E. et al. (1995) Am. J. Med. Genet. 60:94 102; Detera-Wadleigh, S. D. et al. (1999) Proc. Natl. Acad. Sci. USA 96:5604 5609; Berrettini, W. H. et al. (1994) Proc. Natl. Acad. Sci. USA 91:5918 5921; Freimer, N. B. et al. (1996) Nat. Genet. 12:436 441; Straub, R. E. et al. (1994) Nat. Genet. 8:291 296; Pekkarinen, P. et al. (1995) Genome Res. 5:105 115; Craddock, N. & Jones, I. (1999) J. Med. Genet. 36:585 594; Craddock, N. & Jones, I. (2001) Br. J. Psychiatry 41:s128-s133). Linkage between bipolar disorder and chromosome 12q23 12q24 has been reported (Green, E. K. et al. (2000) Am. J. Med. Genet. 96:545; Morissette, J. et al. (1999) Am. J. Med. Genet. 88: 567 587; Ewald, H. et al. (1998) Psychiatr. Genet. 8:131 140 (1998); Degan, B. et al. (2001) Mol. Psychiatry 6:450 455; Detera-Wadleigh, S. D. et al. (1999) Am. J. Med. Genet. 88:255 259; Jacobsen, N. et al. (1996) Psych. Genet. 6:195 199; Rice, J. P. et al. (1997) Am. J. Med. Genet. 74:247 253).

In view of the importance of early diagnosis of depression, there is a need to identify genes associated with depression for diagnostic and therapeutic purposes.

SUMMARY OF THE INVENTION

This invention is based on the discovery of the first evidence implicating specific mutations in the APAF1 gene with susceptibility to depression. The inventors have discovered that mutations in APAF1 which segregate with major depression correlate to an enhancement in caspase activation in apoptosome reconstitution assays.

In a first aspect of the invention, a method for detecting in an individual a susceptibility to depression is provided. Thus, the present invention provides methods for determining whether a subject is at risk for developing depression due to a mutation in the APAF1 gene. This method relies on the fact that mutations in the APAF1 have been correlated by the inventors with the disease. It will be understood by those of skill in the art, given the disclosure of the invention that such mutations are associated with a susceptibility to depression, that a variety of methods can be utilized to detect mutations in the APAF1 gene, including the mutations disclosed herein, which are associated with a susceptibility to depression.

The method can include detecting, in a tissue of the subject, the presence or absence of a polymorphism of the APAF1 gene. The detection of a polymorphism in the APAF1 gene can include ascertaining the existence of at least one of: a deletion of one or more nucleotides; an addition of one or more nucleotides, a substitution of one or more nucleotides; a gross chromosomal rearrangement; an alteration in the level of a messenger RNA transcript; the presence of a non-wild type splicing pattern of a messenger RNA transcript; a non-wild type level of an APAF1 protein; and/or an aberrant level of an APAF1 protein.

For example, detecting the polymorphism can include (i) providing a probe/primer comprised of an oligonucleotide which hybridizes to a sense or antisense sequence of an APAF1 gene or naturally occurring mutants thereof, or 5' or 3' flanking sequences naturally associated with an APAF1 gene; (ii) contacting the probe/primer to an appropriate nucleic acid containing sample; and (iii) detecting, by hybridization of the probe/primer to the nucleic acid, the presence or absence of the polymorphism; e.g. wherein detecting the polymorphism comprises utilizing the probe/primer to determine the nucleotide sequence of an APAF1 gene and, optionally, of the flanking nucleic acid sequences. For instance, the primer can be employed in a polymerase chain reaction (PCR), in a ligase chain reaction (LCR) or other amplification reactions known to a skilled artisan. In alternate embodiments, the level of an APAF1 protein is detected in an immunoassay using an antibody which is specifically immunoreactive with the APAF1 protein. In another embodiment, antibodies specific to APAF1 mutants are used to determine the APAF1 for diagnostic purposes.

In a second aspect of the invention, compounds that are agonists or antagonists of a normal (functional) APAF1 bioactivity and their use in preventing or treating depression are provided. For example, to ameliorate disease symptoms involving insufficient expression of an APAF1 gene and/or inadequate amount of functional APAF1 bioactivity in a subject, a gene therapeutic (comprising a gene encoding a functional APAF1 protein) or a protein therapeutic (comprising a functional APAF1 protein or fragment thereof) can be administered to the subject. Alternatively, agonists or antagonists of APAF1 function (wild-type or mutant) or an APAF1 receptor or a receptor for fragments of APAF1 can be administered.

In a third aspect of the invention, compounds that are antagonists of a disease causing APAF1 bioactivity and their use in preventing or treating depression are provided. For example, to ameliorate disease symptoms involving expression of a mutant APAF1 gene or aberrant expression of a normal APAF1 gene in a subject, a therapeutically effective amount of an antisense, ribozyme, siRNA, or triple helix molecule to reduce or prevent gene expression may be administered to the subject. Alternatively, to ameliorate disease symptoms involving the regulation via an APAF1 protein or APAF1 protein fragments of an upstream or downstream element in an APAF1 mediated biochemical pathway (e.g., signal transduction), a therapeutically effective amount of an agonist or antagonist compound (e.g., small molecule, peptide, peptidomimetic, protein or antibody) that can prevent normal binding of the wild-type APAF1 protein, can induce a therapeutic effect.

In fourth aspect of the invention, assays, e.g., for screening test compounds to identify antagonists (e.g. inhibitors), or alternatively, agonists (e.g. potentiators), of an interaction between an APAF1 protein and, for example, a protein or nucleic acid that binds to the APAF1 protein or fragments of APAF1 are provided. An exemplary method includes the steps of (i) combining an APAF1 polypeptide or bioactive fragments thereof, an APAF1 target molecule (such as an APAF1 ligand or nucleic acid), and a test compound, e.g., under conditions wherein, but for the test compound, the APAF1 protein and APAF1 target molecule are able to interact; and (ii) detecting the formation of a complex which includes the APAF1 protein and the target molecule either by directly quantitating the complex or by measuring inductive effects of the APAF1 protein or fragments of APAF1 protein. A statistically significant change, such as a decrease, in the interaction of the APAF1 and APAF1 target molecule in the presence of a test compound (relative to what is detected in the absence of the test compound) is indicative of a modulation (e.g., inhibition or potentiation of the interaction between the APAF1 protein or fragments of the APAF1 protein and the target molecule).

In a fifth aspect, the present invention provides methods for modulating the transcription of certain genes in a cell by modulating APAF1 bioactivity, (e.g., by potentiating or disrupting an APAF1 bioactivity). In general, whether carried out in vivo, in vitro, or in situ, the method comprises treating the cell with an effective amount of an APAF1 therapeutic (agonist or antagonist of an APAF1 bioactivity) so as to alter, relative to the cell in the absence of treatment, the level of transcription of certain genes. Accordingly, the method can be carried out with APAF1 therapeutics such as peptide and peptidomimetics or other molecules identified in the above-referenced drug screens which agonize or antagonize the effects of an APAF1 bioactivity (e.g. transcription) of a gene which is regulated by an APAF1 protein. Other APAF1 therapeutics include antisense or siRNA constructs for inhibiting expression of APAF1 proteins, and dominant negative mutants of APAF1 proteins which competitively inhibit interactions between ligands (e.g. proteins) and nucleic acids upstream and downstream of the wild-type APAF1 protein.

In a sixth aspect, the invention relates to isolated nucleic acids encoding an altered APAF1. In particular, the invention provides an isolated altered APAF1 nucleic acid, having one or more of the following alterations (in reference to nucleotides 1 to 3744 set forth SEQ ID: 1): (a) the C at nucleotide position 1350 is substituted with G, or a complement thereof; (b) the A at nucleotide position 1394 is substituted with G, or a complement thereof; (c) the G at nucleotide position 2329 is substituted with A, or a complement thereof; (d) the A at nucleotide position 2345 is substituted with C, or a complement thereof; (e) the A at nucleotide position 2857 is substituted with G, or a complement thereof; (f) a T is inserted after nucleotide position 1299, or a complement thereof; (g) the T at nucleotide position 1244 is substituted with C, or a complement thereof; (h) the C at nucleotide position 1070 is substituted with T, or a complement thereof; (i) the C at nucleotide position 1437 is substituted with G, or a complement thereof; and (j) the A at nucleotide position 1874 is substituted with C, or a complement thereof.

In a seventh aspect, the invention provides a nucleic acid probe specifically hybridizable to a human altered APAF1 and not to the corresponding wild-type DNA. According to one embodiment of this aspect of the invention, the altered APAF1 comprises an alteration of SEQ ID NO:1 selected from C1350G, A1394G, G2329A, A2345C, A2857G, insertion of a T after nucleotide position 1299, T1244C, C1070T, C1437G, A1874C or complements thereof.

In an eighth aspect, the invention provides a method for diagnosing an alteration which causes depression by hybridizing a probe to an altered (mutant) APAF1 nucleic acid in a patient's sample of DNA or RNA under stringent conditions which allows hybridization of the probe to nucleic acid comprising the alteration but prevents hybridization of the probe to a wild-type nucleic acid. The presence of a hybridization signal indicates the presence of the alteration. In a preferred embodiment of this aspect of the invention, the method is performed using nucleic acid microchip technology.

In a ninth aspect, the invention provides an isolated altered APAF1 polypeptide. According to this aspect of the invention, the isolated polypeptide has (in reference to SEQ ID NO:2): (a) the Cys at position 450 substituted with Trp; (b) the Gln at position 465 substituted with Arg; (c) the Glu at position 777 substituted with Lys; (d) the Asn at position 782 substituted with Thr; (e) the Thr at position 953 substituted with Ala; (f) the Leu at position 415 substituted with Pro; (g) the Ser at position 357 substituted with Leu; (h) the Asp at position 479 substituted with Glu; or (i) the Glu at position 625 substituted with Ala. In one embodiment of this aspect of the invention, the invention provides a protein molecule comprising the amino acids set forth in SEQ ID NO:3. In another embodiment of this aspect of the invention an antibody capable of binding the altered polypeptide but incapable of binding a wild-type APAF1 polypeptide is provided.

In a tenth aspect, the invention provides a method for detecting an alteration in APAF1 that is associated with depression in a human. Accordingly, the method comprises analyzing an APAF1 gene or an APAF1 gene expression product from cells or tissue of a human. In some embodiments, the mutation is detected by immunoblotting, immunocytochemistry, assaying for binding interactions between the gene product isolated from the tissue and a binding partner capable of specifically binding the polypeptide expression product of a mutant allele and/or a binding partner for the polypeptide, or assaying for the inhibition of biochemical activity of the binding partner. In another embodiment of this aspect of the invention, the method involves comparing the sequence of a subject APAF1 gene with the sequence of one or more wild-type APAF1 gene sequences. According to other embodiments of this aspect of the invention, the mutation can be detected by any method including: (a) hybridizing a probe specific for one of the alterations to RNA isolated from the human sample and detecting the presence of a hybridization product, wherein the presence of the product indicates the presence of the alteration in the sample; (b) hybridizing a probe specific for one of the alterations to cDNA made from RNA isolated from the sample and detecting the presence of a hybridization product, wherein the presence of the product indicates the presence of the alteration in the sample; (c) hybridizing a probe specific for one of the alterations to genomic DNA isolated from the sample and detecting the presence of a hybridization product, wherein the presence of the product indicates the presence of the alteration in the sample; (d) amplifying all or part of the gene in the sample using a set of primers to produce amplified nucleic acids and sequencing the amplified nucleic acids; (e) amplifying part of the gene in the sample using a primer specific for one of the alterations and detecting the presence of an amplified product, wherein the presence of the product indicates the presence of the alteration in the sample; (f) molecularly cloning all or part of the gene in the sample to produce a cloned nucleic acid and sequencing the cloned nucleic acid; (g) amplifying the gene to produce amplified nucleic acids, hybridizing the amplified nucleic acids to a DNA probe specific for one of the alterations and detecting the presence of a hybridization product, wherein the presence of the product indicates the presence of the alteration; (h) forming single-stranded DNA from a gene fragment of the gene from the human sample and single-stranded DNA from a corresponding fragment of a wild-type gene, electrophoresing the single-stranded DNAs on a non-denaturing polyacrylamide gel and comparing the mobility of the single-stranded DNAs on the gel to determine if the single-stranded DNA from the sample is shifted relative to wild-type and sequencing the single-stranded DNA having a shift in mobility; (i) forming a heteroduplex consisting of a first strand of nucleic acid selected from the group consisting of a genomic DNA fragment isolated from the sample, an RNA fragment isolated from the sample and a cDNA fragment made from mRNA from the sample and a second strand of a nucleic acid consisting of a corresponding human wild-type gene fragment, analyzing for the presence of a mismatch in the heteroduplex, and sequencing the first strand of nucleic acid having a mismatch; (j) forming single-stranded DNA from the gene of the human sample and from a corresponding fragment of an allele specific for one of the alterations, electrophoresing the single-stranded DNAs on a non-denaturing polyacrylamide gel and comparing the mobility of the single-stranded DNAs on the gel to determine if the single-stranded DNA from the sample is shifted relative to the allele, wherein no shift in electrophoretic mobility of the single-stranded DNA relative to the allele indicates the presence of the alteration in the sample; and (k) forming a heteroduplex consisting of a first strand of nucleic acid selected from the group consisting of a genomic DNA fragment of the gene isolated from the sample, an RNA fragment isolated from the sample and a cDNA fragment made from mRNA from the sample and a second strand of a nucleic acid consisting of a corresponding gene allele fragment specific for one of the alterations and analyzing for the presence of a mismatch in the heteroduplex, wherein no mismatch indicates the presence of the alteration.

In an eleventh aspect, the invention provides a method for determining whether a human subject has or is at risk for developing depression. In one embodiment, the method involves: (a) obtaining a sample from a subject, said sample comprising nucleic acid molecules containing APAF1 gene; and (b) detecting the presence or absence of a genetic alteration in the gene of said subject, wherein the presence of said genetic alteration identifies a subject that has or is at risk for developing depression. In another embodiment, the alteration (mutation) is selected from the group consisting of C1350G, A1394G, G2329A, A2345C, A2857G, insertion of a T after nucleotide position 1299, T1244C, C1070T, C1437G, A1874C or complements thereof (referring to SEQ ID NO: 1).

In a twelfth aspect, the invention provides a method for preventing or treating depression in a subject which comprises administering to the subject a therapeutically effective amount of a compound that agonizes or antagonizes wild-type APAF1, or agonizes or antagonizes altered APAF1, or agonizes or antagonizes an APAF1 receptor. In one embodiment, the method for preventing or treating depression involves a compound is selected from: (a) a drug; (b) an antisense molecule; (c) an siRNA molecule; (d) a ribozyme; (e) a triplex molecule; (f) wild-type APAF1 nucleic acid; (g) wild-type APAF1 protein; (h) a protein which binds wild-type or altered APAF1 protein; (i) a peptidomimetic; (j) a non-peptide, non-nucleic acid small molecule; and (k) an antibody.

In a thirteenth aspect, the invention provides a non-human animal which carries an altered APAF1 allele in its genome. According to one embodiment of this aspect of the invention, a cell line isolated from the non-human animal is provided.

In a fourteenth aspect, the invention provides a method of screening for drug candidates useful in treating depression resulting from an alteration in APAF1. The method, according to one embodiment, involves mixing a mutant APAF1 in both the presence of a drug and the absence of the drug and measuring the level of the biological activity of the mutant APAF1. If the level of the biological activity is less in the presence of the drug than in the absence of the drug then it is a drug candidate for treating depression. According to another embodiment of this aspect of the invention, the method involves treating an animal, which is heterozygous or homozygous for APAF1 containing an alteration, with a drug. If the animal does not develop depression, or symptoms thereof, then the drug is a candidate for treating depression. In yet another embodiment of this aspect of the invention, a method for screening potential depression therapeutics is provided. The method according to this embodiment involves combining an APAF1 binding partner and a compound suspected of being a depression therapeutic and measuring the biological activity of the binding partner.

BRIEF DESCRIPTION OF THE DRAWINGS

FIG. 3 indicates that mutations in Apaf-1 that segregate with depression result in increased activation of caspase-9.

DETAILED DESCRIPTION OF THE INVENTION

Figure 1:
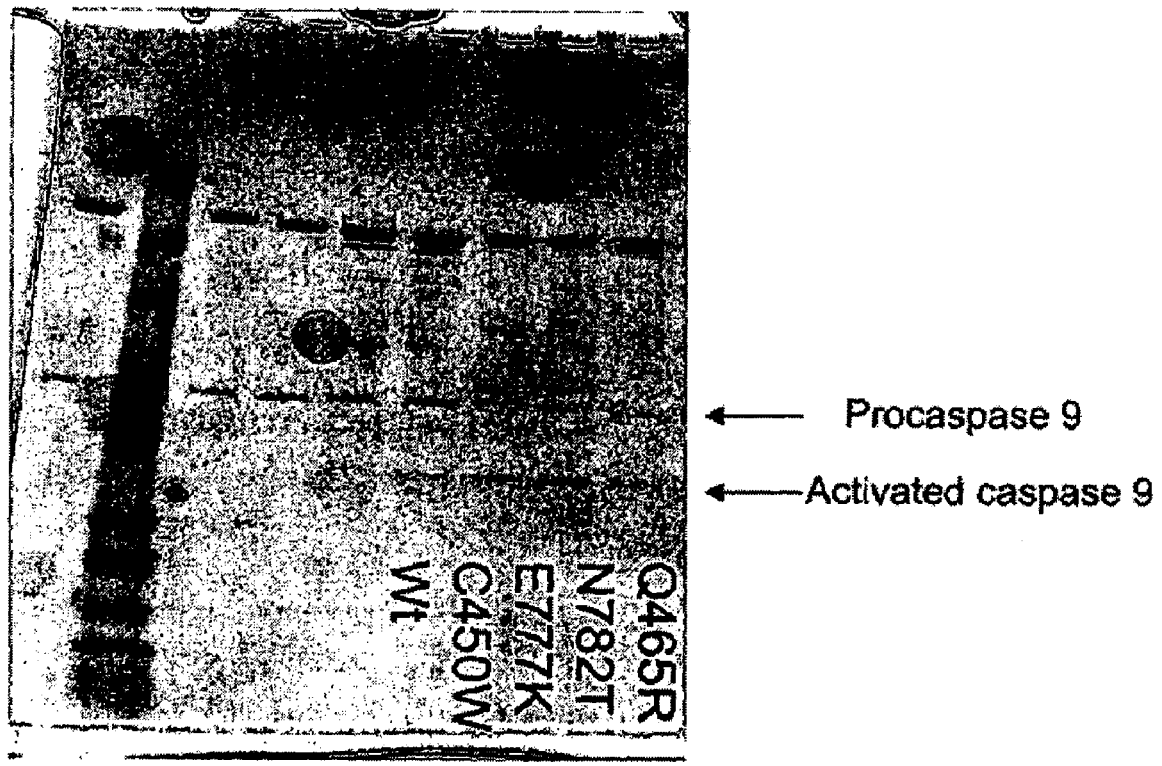
FIG. 1 shows a SDS-PAGE gel demonstrating that APAF1 mutants segregating with depression are capable of reconstituting apoptosome activity. See Example 2 for experimental details. Experiment performed at 0.3 mM [caspase], 0.3 or 0.6 mM [Apaf-1], 0.3 mM cytochrome C. Conversion of pro-caspase-9 to caspase 9 is clearly evident as indicated by the bands at the arrows.

The present invention is based in part on the discovery of polymorphisms in the APAF1 gene which are linked to depression. Five different missense changes were discovered in linked families in this gene which result in a Cys->Trp substitution at amino acid 450 (C450W) in family 8546 (nucleotide change c1350g), a Gln->Arg substitution at amino acid 465 (Q465R) in family 8428 (nucleotide change a1394g), a Glu->Lys substitution at amino acid 777 (E777K) in family 8347.2 (nucleotide change g2329a), an Asn->Thr substitution at amino acid 782 (A782T) in family 8288 (nucleotide change a2345c) and a Thr->Ala substitution at amino acid 953 (T953A) in family 8828803 (nucleotide change a2857g). Further analysis of APAF1 has uncovered three other mutations corresponding to Ser357Leu; Asp479Glu; and Glu625Ala with respective nucleotide changes are C1070T; C1437G; and A1874C. Each one occurs on a haplotype that segregates into more than one affected individual. Additional 180 male affected cases were examined. To date one frameshift mutation 1299insT (inserts stop codon at codon 439) in family 8205 and another missense change Leu->Pro at amino acid 415 (L415P) in family 8582 (nucleotide change t1244c), were discovered in this random case set. Neither of these changes were seen in 177 control samples. The protein encoded by the frameshift mutation is set forth in SEQ ID NO:3. Based on these findings, the invention provides therapeutic methods, compositions and diagnostics for depression based on APAF1.

The cDNA for the APAF1 gene and the protein sequence are set forth in GenBank accession number AF149794. The coding sequence for APAF1 as used herein is shown in SEQ ID NO:1. The corresponding amino acid sequence for APAF1 is set forth in SEQ ID NO:2. The present invention relates to APAF1 agonists and antagonists and their use in treating depression. For example, (i) nucleic acid molecules encoding functional APAF1 protein; (ii) nucleic acids that are effective antisense, siRNA, ribozyme and triplex antagonists of nucleic acids encoding functional APAF1 protein; (iii) functional APAF1 proteins or peptides; (iv) anti-APAF1 antibodies; (v) drugs affecting wild-type or mutant APAF1 function or APAF1 interaction with an APAF1 receptor (or interacting partner) and preparations of such compositions are disclosed herein. In addition, the invention provides drug discovery assays for identifying additional agents that agonize or antagonize the biological function of APAF1 protein (e.g. by altering the interaction of APAF1 molecules with either downstream or upstream elements in the biochemical (e.g. signal transduction) pathway). Moreover, the present invention provides assays for diagnosing whether a subject has depression or has a predisposition towards developing depression.

Proof that any particular gene located within the genetically defined interval is a disease susceptibility locus is obtained by finding sequences in DNA or RNA extracted from affected kindred members which create abnormal gene products or abnormal levels of gene product. Such disease susceptibility alleles will co-segregate with the disease in large kindreds. They will also be present at a much higher frequency in non-kindred individuals with the disease than in individuals in the general population. In identifying a disease susceptibility locus, the key is to find polymorphisms or mutations which are serious enough to cause obvious disruption to the normal function of the gene product. These mutations can take a number of forms. The most severe forms are typically frame shift mutations or large deletions which cause the gene to code for an abnormal protein or one which significantly alters protein expression. Less severe disruptive mutations include small in-frame deletions and non-conservative base pair substitutions which have a significant effect on the protein produced, such as changes to or from a cysteine residue, from a basic to an acidic amino acid or vice versa, from a hydrophobic to hydrophilic amino acid or vice versa, or other mutations which affect secondary, tertiary or quaternary protein structure. Small deletions or base pair substitutions can also significantly alter protein expression by changing the level of transcription, splice pattern, mRNA stability, or translation efficiency of the gene transcript. Silent mutations or those resulting in conservative amino acid substitutions are not generally expected to disrupt protein function. Causal mutations can also be found in the promoter of the gene. These mutations interfere with the binding of regulatory factors and in this way alter transcription of the gene and therefore change the function of the gene. Since the inventors have discovered that APAF1 mutations segregate with major depression, Applicants contemplate that the abovementioned classes of mutations can occur in APAF1 and be associated with depression.

Diagnostics

The discovery by the present inventors that APAF1 mutations segregate with depression now allows for depression susceptibility testing based on detecting mutations in APAF1.

In one aspect, the invention features probes and primers for use in a prognostic or diagnostic assay. For instance, the present invention also provides a probe/primer comprising a substantially purified oligonucleotide, which oligonucleotide comprises a region of nucleotide sequence that hybridizes under stringent conditions to at least approximately 12, preferably 25, more preferably 40, 50 or 75 consecutive nucleotides of sense or antisense sequence of APAF1, including 5' and/or 3' untranslated regions. In preferred embodiments, the probe further comprises a detectable label group attached thereto, e.g. the label group is selected from amongst radioisotopes, fluorescent compounds, enzymes, and enzyme co-factors. The selection of probes and primers for diagnosis of a susceptibility of depression (i.e, detection of APAF1 mutations) is within the capability of the skilled artisan apprised of the invention.

In a further aspect, the present invention features methods for determining whether a subject is at risk for developing depression. According to the diagnostic and prognostic methods of the present invention, alteration of the wild-type APAF1 locus is detected. "Alteration of a wild-type gene" encompasses all forms of mutations including deletions, insertions and point mutations in the coding and non-coding regions. Deletions may be of the entire gene or of only a portion of the gene. Point mutations may result in stop codons, frameshift mutations or amino acid substitutions. Point mutations or deletions in the promoter can change transcription and thereby alter the gene function. Somatic mutations are those which occur only in certain tissues and are not inherited in the germline. Germline mutations can be found in any of a body's tissues and are inherited. The finding of APAF1 germline mutations thus provides diagnostic information. An APAF1 allele which is not deleted (e.g., found on the sister chromosome to a chromosome carrying an APAF1 deletion) can be screened for other mutations, such as insertions, small deletions, and point mutations. Point mutational events may occur in regulatory regions, such as in the promoter of the gene, or in intron regions or at intron/exon junctions.

Useful diagnostic techniques include, but are not limited to fluorescent in situ hybridization (FISH), direct DNA sequencing, PFGE (pulsed-field gel electrophoresis) analysis, Southern blot analysis, single stranded conformation analysis (SSCA), RNase protection assay, allele-specific oligonucleotide (ASO), dot blot analysis and PCR-SSCP, as discussed in detail further below. Also useful is the recently developed technique of DNA microchip technology. In addition to the techniques described herein, similar and other useful techniques are also described in U.S. Pat. Nos. 5,837,492 and 5,800,998, each incorporated herein by reference.

Predisposition to disease can be ascertained by testing any tissue of a human for mutations of the APAF1 gene. For example, a person who has inherited a germline APAF1 mutation may be prone to developing depression. This can be determined by testing DNA from any tissue of the person's body. Most simply, blood can be drawn and DNA extracted from the cells of the blood. In addition, prenatal diagnosis can be accomplished by testing fetal cells, placental cells or amniotic cells for mutations of the APAF1 gene. Alteration of a wild-type APAF1 allele, whether, for example, by point mutation or deletion, can be detected by any of the means discussed herein.

There are several methods that can be used to detect DNA sequence variation. Direct DNA sequencing, either manual sequencing or automated fluorescent sequencing can detect sequence variation. Another approach is the single-stranded conformation polymorphism assay (SSCA) (Orita, et al. (1989) Proc. Natl. Acad. Sci. USA 86:2776 2770). This method does not detect all sequence changes, especially if the DNA fragment size is greater than 200 bp, but can be optimized to detect most DNA sequence variation. The reduced detection sensitivity is a disadvantage, but the increased throughput possible with SSCA makes it an attractive, viable alternative to direct sequencing for mutation detection on a research basis. The fragments which have shifted mobility on SSCA gels are then sequenced to determine the exact nature of the DNA sequence variation. Other approaches based on the detection of mismatches between the two complementary DNA strands include clamped denaturing gel electrophoresis (CDGE) (Sheffield, V. C., et al. (1991) Am. J. Hum. Genet. 49:699 706), heteroduplex analysis (HA) (White, M. B., et al., (1992) Genomics 12:301 306) and chemical mismatch cleavage (CMC) (Grompe, M., et al., (1989) Proc. Natl. Acad. Sci. USA 86:5855 5892). None of the methods described above will detect large deletions, duplications or insertions, nor will they detect a regulatory mutation which affects transcription or translation of the protein. Other methods which can detect these classes of mutations such as a protein truncation assay or the asymmetric assay, detect only specific types of mutations and would not detect missense mutations. A review of currently available methods of detecting DNA sequence variation can be found in a recent review by Grompe, M., (1993) Nature Genetics 5:111 117. Once a mutation is known, an allele specific detection approach such as allele specific oligonucleotide (ASO) hybridization can be utilized to rapidly screen large numbers of other samples for that same mutation.

Detection of point mutations may be accomplished by molecular cloning of the APAF1 allele(s) and sequencing the allele(s) using techniques well known in the art. Alternatively, the gene sequences can be amplified directly from a genomic DNA preparation from the tissue or cells, using known techniques. The DNA sequence of the amplified sequences can then be determined.

There are six well known methods for a more complete, yet still indirect, test for confirming the presence of a susceptibility allele: 1) single-stranded conformation analysis (SSCA) (Orita, et al. (1989) Proc. Natl. Acad. Sci. USA 86:2776 2770); 2) denaturing gradient gel electrophoresis (DGGE) (Wartell, R. M., et al. (1990) Nucl. Acids Res. 18:2699 2705; Sheffield, V. C., et al. (1989) Proc. Natl. Acad. Sci. USA 86:232 236); 3) RNase protection assays (Finkelstein, J., et al. (1990) Genomics 7:167 172; Kinszler, K. W., et al. (1991) Science 251:1366 1370); 4) allele-specific oligonucleotides (ASOs) (Conner, B. J., et al. (1983) Proc. Natl. Acad. Sci. USA 80:278 282); 5) the use of proteins which recognize nucleotide mismatches, such as the E. coli mutS protein (Modrich, P. (1991) Ann. Rev. Genet. 25:229 253); and 6) allele-specific PCR (Rano & Kidd (1989) Nucl. Acids Res. 17:8392). For allele-specific PCR, primers are used which hybridize at their 3' ends to a particular APAF1 mutation. If the particular APAF1 mutation is not present, an amplification product is not observed. Amplification Refractory Mutation System (ARMS) can also be used, as disclosed in European Patent Application Publication No. 0332435 and in Newton, C. R., et al. (1989) Nucl. Acids Res. 17:2503 2516. Insertions and deletions of genes can also be detected by cloning, sequencing and amplification. In addition, restriction fragment length polymorphism (RFLP) probes for the gene or surrounding marker genes can be used to score alteration of an allele or an insertion in a polymorphic fragment. Such a method is particularly useful for screening relatives of an affected individual for the presence of the APAF1 mutation found in that individual. Other techniques for detecting insertions and deletions as known in the art can be used.

In the first three methods (SSCA, DGGE and RNase protection assay), a new electrophoretic band appears. SSCA detects a band which migrates differentially because the sequence change causes a difference in single-strand, intramolecular base pairing. RNase protection involves cleavage of the mutant polynucleotide into two or more smaller fragments. DGGE detects differences in migration rates of mutant sequences compared to wild-type sequences, using a denaturing gradient gel. In an allele-specific oligonucleotide assay, an oligonucleotide is designed which detects a specific sequence, and the assay is performed by detecting the presence or absence of a hybridization signal. In the mutS assay, the protein binds only to sequences that contain a nucleotide mismatch in a heteroduplex between mutant and wild-type sequences.

Mismatches, according to the present invention, are hybridized nucleic acid duplexes in which the two strands are not 100% complementary. Lack of total homology may be due to deletions, insertions, inversions or substitutions. Mismatch detection can be used to detect point mutations in the gene or in its mRNA product. While these techniques are less sensitive than sequencing, they are simpler to perform on a large number of tumor samples. An example of a mismatch cleavage technique is the RNase protection method. In the practice of the present invention, the method involves the use of a labeled riboprobe which is complementary to the human wild-type APAF1 gene coding sequence. The riboprobe and either mRNA or DNA isolated from the tumor tissue are annealed (hybridized) together and subsequently digested with the enzyme RNase A which is able to detect some mismatches in a duplex RNA structure. If a mismatch is detected by RNase A, it cleaves at the site of the mismatch. Thus, when the annealed RNA preparation is separated on an electrophoretic gel matrix, if a mismatch has been detected and cleaved by RNase A, an RNA product will be seen which is smaller than the full length duplex RNA for the riboprobe and the mRNA or DNA. The riboprobe need not be the full length of the APAF1 mRNA or gene but can be a segment of either. If the riboprobe comprises only a segment of the APAF1 mRNA or gene, it will be desirable to use a number of these probes to screen the whole mRNA sequence for mismatches.

In similar fashion, DNA probes can be used to detect mismatches, through enzymatic or chemical cleavage. See, e.g., Cotton, et al. (1988) Proc. Natl. Acad. Sci. USA 85:4397 4401; Shenk, et al. (1975) Proc. Natl. Acad. Sci. USA 72:989; and Novack, et al. (1986) Proc. Natl. Acad. Sci. USA 83:586. Alternatively, mismatches can be detected by shifts in the electrophoretic mobility of mismatched duplexes relative to matched duplexes. See, e.g., Cariello (1988) Human Genetics 42:726. With either riboprobes or DNA probes, the cellular mRNA or DNA which might contain a mutation can be amplified using PCR before hybridization. Changes in DNA of the APAF1 gene can also be detected using Southern hybridization, especially if the changes are gross rearrangements, such as deletions and insertions.

DNA sequences of the APAF1 gene which have been amplified by use of PCR may also be screened using allele-specific probes. These probes are nucleic acid oligomers, each of which contains a region of the APAF1 gene sequence harboring a known mutation. For example, one oligomer may be about 30 nucleotides in length (although shorter and longer oligomers are also usable as well recognized by those of skill in the art), corresponding to a portion of the APAF1 gene sequence. By use of a battery of such allele-specific probes, PCR amplification products can be screened to identify the presence of a previously identified mutation in the APAF1 gene. Hybridization of allele-specific probes with amplified APAF1 sequences can be performed, for example, on a nylon filter. Hybridization to a particular probe under high stringency hybridization conditions indicates the presence of the same mutation in the tumor tissue as in the allele-specific probe.

The newly developed technique of nucleic acid analysis via microchip technology is also applicable to the present invention. In this technique, literally thousands of distinct oligonucleotide probes are built up in an array on a silicon chip. Nucleic acid to be analyzed is fluorescently labeled and hybridized to the probes on the chip. It is also possible to study nucleic acid-protein interactions using these nucleic acid microchips. Using this technique one can determine the presence of mutations, sequence the nucleic acid being analyzed, and/or one can measure expression levels of a gene of interest. The method is one of parallel processing of many, even thousands, of probes at once and can tremendously increase the rate of analysis. Several papers have been published which use this technique. See, e.g., Hacia J G, et al. (1996) Nature Genetics 14:441 447; Shoemaker D D, et al. (1996) Nature Genetics 14:450 456; Chee, M., et al. (1996) Science 274:610 614; Lockhart D J, et al. (1996) Nature Biotechnology 14:1675 1680; DeRisi, J., et al. (1996) Nat. Genet. 14:457 460; Lipshutz R J, et al. (1995) BioTechniques 19:442 447. This method has already been used to screen people for mutations in the breast cancer gene BRCA1 (Hacia, J G, et al. (1996) Nature Genetics 14:441 447). This new technology has been reviewed in a news article in Chemical and Engineering News (Borman, S. (1996) Chemical & Engineering News, December 9 issue, pp. 42 43) and been the subject of an editorial (Nature Genetics, 1996). Also see Fodor, S. P. A. (1997) Science 277:393 395.

The most definitive test for mutations in a candidate locus is to directly compare genomic APAF1 sequences from disease patients with those from a control population. Alternatively, one could sequence messenger RNA after amplification, e.g., by PCR, thereby eliminating the necessity of determining the exon structure of the candidate gene.

Mutations from disease patients falling outside the coding region of APAF1 can be detected by examining the non-coding regions, such as introns and regulatory sequences near or within the APAF1 gene. An early indication that mutations in non-coding regions are important can come from Northern blot experiments that reveal messenger RNA molecules of abnormal size or abundance in disease patients as compared to control individuals.

Alteration of APAF1 mRNA expression can be detected by any techniques known in the art. These include Northern blot analysis, PCR amplification and RNase protection. Diminished or increased mRNA expression indicates an alteration of the wild-type APAF1 gene. Alteration of wild-type APAF1 genes can also be detected by screening for alteration of wild-type APAF1 protein. For example, monoclonal antibodies immunoreactive with APAF1 can be used to screen a tissue. Lack of cognate antigen would indicate an APAF1 mutation. Antibodies specific for products of mutant alleles could also be used to detect mutant APAF1 gene product. Such immunological assays can be done in any convenient formats known in the art. These include Western blots, immunohistochemical assays and ELISA assays. Any means for detecting an altered APAF1 protein can be used to detect alteration of wild-type APAF1 genes. Functional assays, such as protein binding determinations, can be used. In addition, assays can be used which detect APAF1 biochemical function. Finding a mutant APAF1 gene product indicates alteration of a wild-type APAF1 gene.

The primer pairs of the present invention are useful for determination of the nucleotide sequence of a particular APAF1 allele using PCR. The pairs of single-stranded DNA primers can be annealed to sequences within or surrounding the APAF1 gene on chromosome 12 in order to prime amplifying DNA synthesis of the APAF1 gene itself. A complete set of these primers allows synthesis of all of the nucleotides of the APAF1 gene coding sequences, i.e., the exons. The set of primers preferably allows synthesis of both intron and exon sequences. Allele-specific primers can also be used. Such primers anneal only to particular APAF1 mutant alleles, and thus will only amplify a product in the presence of the mutant allele as a template.

In order to facilitate subsequent cloning of amplified sequences, primers may have restriction enzyme site sequences appended to their 5' ends. Thus, all nucleotides of the primers are derived from APAF1 sequences or sequences adjacent to APAF1, except for the few nucleotides necessary to form a restriction enzyme site. Such enzymes and sites are well known in the art. The primers themselves can be synthesized using techniques which are well known in the art. Generally, the primers can be made using oligonucleotide synthesizing machines which are commercially available. Given the known sequences of the APAF1 exons and the 5' alternate exon, the design of particular primers is well within the skill of the art. Suitable primers for mutation screening are also described herein.

The nucleic acid probes provided by the present invention are useful for a number of purposes. They can be used in Southern hybridization to genomic DNA and in the RNase protection method for detecting point mutations already discussed above. The probes can be used to detect PCR amplification products. They can also be used to detect mismatches with the APAF1 gene or mRNA using other techniques.

It has been discovered that individuals with the wild-type APAF1 gene do not have depression which results from the APAF1 allele. However, mutations which interfere with the function of the APAF1 protein are involved in the susceptibility to depression as shown herein. Thus, the presence of an altered (or a mutant) APAF1 gene which produces a protein having a loss of function, or altered function, directly correlates to an increased risk of disease. In order to detect an APAF1 gene mutation, a biological sample is prepared and analyzed for a difference between the sequence of the APAF1 allele being analyzed and the sequence of the wild-type APAF1 allele. Mutant APAF1 alleles can be initially identified by any of the techniques described above. The mutant alleles are then sequenced to identify the specific mutation of the particular mutant allele. Alternatively, mutant APAF1 alleles can be initially identified by identifying mutant (altered) APAF1 proteins, using conventional techniques. The mutant alleles are then sequenced to identify the specific mutation for each allele. The mutations, especially those which lead to an altered function of the APAF1 protein, are then used for the diagnostic methods of the present invention.

The present invention employs definitions commonly used in the art with specific reference to the gene described in the present application. Such definitions can be found in U.S. Pat. Nos. 5,837,492; 5,800,998; 6,261,801; 6,274,720 and 6,274,376, each incorporated herein by reference. Such definitions are employed herein unless the context indicates otherwise.

Nucleic Acids and Proteins

A nucleic acid or fragment thereof has substantial identity with another if, when optimally aligned (with appropriate nucleotide insertions or deletions) with the other nucleic acid (or its complementary strand), there is nucleotide sequence identity in at least about 60% of the nucleotide bases, usually at least about 70%, more usually at least about 80%, preferably at least about 90%, and more preferably at least about 95 98% of the nucleotide bases. A protein or fragment thereof has substantial identity with another if, optimally aligned, there is an amino acid sequence identity of at least about 30% identity with an entire naturally-occurring protein or a portion thereof, usually at least about 70% identity, more usually at least about 80% identity, preferably at least about 90% identity, and more preferably at least about 95% identity.

Identity means the degree of sequence relatedness between two polypeptide or two polynucleotide sequences as determined by the identity of the match between two strings of such sequences, such as the full and complete sequence. Identity can be readily calculated. While there exist a number of methods to measure identity between two polynucleotide or polypeptide sequences, the term "identity" is well known to skilled artisans (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991). Methods commonly employed to determine identity between two sequences include, but are not limited to, those disclosed in Guide to Huge Computers, Martin J. Bishop, ed., Academic Press, San Diego, 1994, and Carillo, H., and Lipman, D., SIAM J Applied Math. 48:1073 (1988). Preferred methods to determine identity are designed to give the largest match between the two sequences tested. Such methods are codified in computer programs. Preferred computer program methods to determine identity between two sequences include, but are not limited to, GCG (Genetics Computer Group, Madison Wis.) program package (Devereux, J., et al., Nucleic Acids Research 12:387 (1984)), BLASTP, BLASTN, FASTA (Altschul, S. F. et al. (1990) J. Mol. Biol. 215:403 410; and Altschul, S. F. et al. (1997) Nucl. Acids Res. 25:3389 3402). The well-known Smith Waterman algorithm may also be used to determine identity.

As an illustration, by a polynucleotide having a nucleotide sequence having at least, for example, 95% "identity" to a reference nucleotide sequence, it is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence can occur at the 5' or 3' terminal positions of the reference nucleotide sequence or anywhere between those terminal positions, interspersed either individually among nucleotides in the reference sequence or in one or more contiguous groups within the reference sequence.

Alternatively, substantial homology or (similarity) exists when a nucleic acid or fragment thereof will hybridize to another nucleic acid (or a complementary strand thereof) under selective hybridization conditions, to a strand, or to its complement. Selectivity of hybridization exists when hybridization which is substantially more selective than total lack of specificity occurs. Typically, selective hybridization occurs when there is at least about 55% homology over a stretch of at least about 14 nucleotides, preferably at least about 65%, more preferably at least about 75%, and most preferably at least about 90%. The length of homology comparison, as described, can be over longer stretches, and in certain embodiments can be over a stretch of at least about nine nucleotides, usually at least about 20 nucleotides, more usually at least about 24 nucleotides, typically at least about 28 nucleotides, more typically at least about 32 nucleotides, and preferably at least about 36 or more nucleotides.

Nucleic acid hybridization can be affected by such conditions as salt concentration, temperature, or organic solvents, in addition to the base composition, length of the complementary strands, and the number of nucleotide base mismatches between the hybridizing nucleic acids, as is readily appreciated by those skilled in the art. Stringent temperature conditions will generally include temperatures in excess of 30° C., typically in excess of 37° C., and preferably in excess of 45° C. Stringent salt conditions will ordinarily be less than 1000 mM, typically less than 500 mM, and preferably less than 200 mM. However, the combination of parameters is much more important than the measure of any single parameter. The stringency conditions are dependent on the length of the nucleic acid and the base composition of the nucleic acid, and can be determined by techniques well known in the art. See, e.g., Ausubel, F. M., et al. (1992) Current Protocols in Molecular Biology, (J. Wiley and Sons, NY); Wetmur, J. G. and Davidson, N. (1968) J. Mol. Biol. 31:349 370.

Thus, as herein used, the term "stringent conditions" means hybridization will occur only if there is at least 95% and preferably at least 97% identity between the sequences. Such hybridization techniques are well known to those of skill in the art. Stringent hybridization conditions are as defined above or, alternatively, conditions under overnight incubation at 42° C. in a solution comprising: 50% formamide, 5×SSC (150 mM NaCl, 15 mM trisodium citrate), 50 mM sodium phosphate (pH7.6), 5×Denhardt's solution, 10% dextran sulfate, and 20 μg/ml denatured, sheared salmon sperm DNA, followed by washing the filters in 0.1×SSC at about 65° C.

The terms "isolated", "substantially pure", and "substantially homogeneous" are used interchangeably to describe a protein or polypeptide which has been separated from components which accompany it in its natural state. A monomeric protein is substantially pure when at least about 60 to 75% of a sample exhibits a single polypeptide sequence. A substantially pure protein can typically comprise about 60 to 90% W/W of a protein sample, more usually about 95%, and preferably can be over about 99% pure. Protein purity or homogeneity can be indicated by a number of means well known in the art, such as polyacrylamide gel electrophoresis of a protein sample, followed by visualizing a single polypeptide band upon staining the gel. For certain purposes, higher resolution can be provided by using HPLC or other means well known in the art which are utilized for purification.

Large amounts of the nucleic acids of the present invention can be produced by (a) replication in a suitable host or transgenic animals or (b) chemical synthesis using techniques well known in the art. Constructs prepared for introduction into a prokaryotic or eukaryotic host may comprise a replication system recognized by the host, including the intended polynucleotide fragment encoding the desired polypeptide, and will preferably also include transcription and translational initiation regulatory sequences operably linked to the polypeptide encoding segment. Expression vectors include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Secretion signals can also be included where appropriate which allow the protein to cross and/or lodge in cell membranes, and thus attain its functional topology, or be secreted from the cell. Such vectors may be prepared by means of standard recombinant techniques well known in the art.

Methods of Use: Nucleic Acid Diagnosis and Diagnostic Kits

In order to detect the presence of an APAF1 allele predisposing an individual to depression, a biological sample such as blood is prepared and analyzed for the presence or absence of predisposing alleles of APAF1. Results of these tests and interpretive information are returned to the health care provider for communication to the tested individual. Such diagnoses can be performed by diagnostic laboratories, or, alternatively, diagnostic kits are manufactured and sold to health care providers or to private individuals for self-diagnosis. Diagnositic or prognostic tests can be performed as described herein or using well known techniques, such as described in U.S. Pat. No. 5,800,998, incorporated herein by reference.

Initially, the screening method can involve amplification of the relevant APAF1 sequences. In another preferred embodiment of the invention, the screening method involves a non-PCR based strategy. Such screening methods include two-step label amplification methodologies that are well known in the art. Both PCR and non-PCR based screening strategies can detect target sequences with a high level of sensitivity.

The most popular method used today is target amplification. Here, the target nucleic acid sequence is amplified with a polymerase. One particularly preferred method using polymerase-driven amplification is the polymerase chain reaction (PCR). The polymerase chain reaction and other polymerase-driven amplification assays can achieve over a million-fold increase in copy number through the use of polymerase-driven amplification cycles. Once amplified, the resulting nucleic acid can be sequenced or used as a substrate for DNA probes.

When the probes are used to detect the presence of the target sequences (for example, in screening for depression susceptibility), the biological sample to be analyzed, such as blood or serum, may be treated, if desired, to extract the nucleic acids. The sample nucleic acid can be prepared in various ways to facilitate detection of the target sequence; e.g. denaturation, restriction digestion, electrophoresis or dot blotting. The targeted region of the analyte nucleic acid usually must be at least partially single-stranded to form hybrids with the targeting sequence of the probe. If the sequence is naturally single-stranded, denaturation will not be required. However, if the sequence is double-stranded, the sequence will probably need to be denatured. Denaturation can be carried out by various techniques known in the art.

Analyte nucleic acid and probe are incubated under conditions which promote stable hybrid formation of the target sequence in the probe with the putative targeted sequence in the analyte. The region of the probes which is used to bind to the analyte can be made completely complementary to the targeted region of human chromosome 12. Therefore, high stringency conditions are desirable in order to prevent false positives. However, conditions of high stringency are used only if the probes are complementary to regions of the chromosome which are unique in the genome. The stringency of hybridization is determined by a number of factors during hybridization and during the washing procedure, including temperature, ionic strength, base composition, probe length, and concentration of formamide. These factors are outlined in, for example, Maniatis T., et al. (1982) Molecular Cloning: A Laboratory Manual (Cold Spring Harbor Laboratory, Cold Spring Harbor, N.Y.) and Sambrook, J., et al. (1989) Molecular Cloning: A Laboratory Manual, 2nd Ed. (Cold Spring Harbor Laboratory, Cold Spring Harbor, N.Y.). Under certain circumstances, the formation of higher order hybrids, such as triplexes, quadraplexes, etc., may be desired to provide the means of detecting target sequences.

Detection, if any, of the resulting hybrid is usually accomplished by the use of labeled probes. Alternatively, the probe may be unlabeled, but may be detectable by specific binding with a ligand which is labeled, either directly or indirectly. Suitable labels, and methods for labeling probes and ligands are known in the art, and include, for example, radioactive labels which may be incorporated by known methods (e.g., nick translation, random priming or kinasing), biotin, fluorescent groups, chemiluminescent groups (e.g., dioxetanes, particularly triggered dioxetanes), enzymes, antibodies and the like. Variations of this basic scheme are known in the art, and include those variations that facilitate separation of the hybrids to be detected from extraneous materials and/or that amplify the signal from the labeled moiety. A number of these variations are reviewed in, e.g., Matthews and Kricka (1988) Anal. Biochem. 169:1; Landegren, et al. (1988) Science 242: 229; Mittlin (1989) Clinical Chem. 35:1819; U.S. Pat. No. 4,868,105, and in EPO Publication No. 225,807.

As noted above, non-PCR based screening assays are also contemplated in this invention. This procedure hybridizes a nucleic acid probe (or an analog such as a methyl phosphonate backbone replacing the normal phosphodiester), to the low level DNA target. This probe can have an enzyme covalently linked to the probe, such that the covalent linkage does not interfere with the specificity of the hybridization. This enzyme-probe-conjugate-target nucleic acid complex can then be isolated away from the free probe enzyme conjugate and a substrate is added for enzyme detection. Enzymatic activity is observed as a change in color development or luminescent output resulting in a $10^3$ $10^6$ increase in sensitivity. For an example relating to the preparation of oligodeoxynucleotide-alkaline phosphatase conjugates and their use as hybridization probes see Jablonski, E., et al. (1986) Nuc. Acids Res. 14:6115 6128.

Two-step label amplification methodologies are known in the art. These assays work on the principle that a small ligand (such as digoxigenin, biotin, or the like) is attached to a nucleic acid probe capable of specifically binding APAF1. Allele specific probes are also contemplated within the scope of this example and exemplary allele specific probes include probes encompassing the predisposing or potentially predisposing mutations summarized in herein.

In one example, the small ligand attached to the nucleic acid probe is specifically recognized by an antibody-enzyme conjugate. In one embodiment of this example, digoxigenin is attached to the nucleic acid probe. Hybridization is detected by an antibody-alkaline phosphatase conjugate which turns over a chemiluminescent substrate. For methods for labeling nucleic acid probes according to this embodiment see Martin et al., 1990. In a second example, the small ligand is recognized by a second ligand-enzyme conjugate that is capable of specifically complexing to the first ligand. A well known embodiment of this example is the biotin-avidin type of interactions. For methods for labeling nucleic acid probes and their use in biotin-avidin based assays see Rigby, P. W. J., et al. (1977) J. Mol. Biol. 113:237 251 and Nguyen, Q., et al. (1992) BioTechniques 13:116 123.

It is also contemplated within the scope of this invention that the nucleic acid probe assays of this invention will employ a cocktail of nucleic acid probes capable of detecting APAF1. Thus, in one example to detect the presence of APAF1 in a cell sample, more than one probe complementary to APAF1 is employed and in particular the number of different probes is alternatively 2, 3, or 5 different nucleic acid probe sequences. In another example, to detect the presence of mutations in the APAF1 gene sequence in a patient, more than one probe complementary to APAF1 is employed where the cocktail includes probes capable of binding to the allele-specific mutations identified in populations of patients with alterations in APAF1. In this embodiment, any number of probes can be used, and can preferably include probes corresponding to the major gene mutations identified as predisposing an individual to depression. Some candidate probes contemplated within the scope of the invention include probes that include the allele-specific mutations identified herein and those that have the APAF1 regions corresponding to SEQ ID NOs:1 5 and 8 both 5' and 3' to the mutation site.

Methods of Use: Peptide Diagnosis and Diagnostic Kits

Susceptibility to depression can also be detected on the basis of the alteration of wild-type APAF1 polypeptide. Peptide diagnostic or prognostic tests can be performed as described herein or using well known techniques, such as described in U.S. Pat. No. 5,800,998, incorporated herein by reference. For example, such alterations can be determined by sequence analysis in accordance with conventional techniques. More preferably, antibodies (polyclonal or monoclonal) are used to detect differences in, or the absence of, APAF1 peptides. The antibodies can be prepared in accordance with conventional techniques. Other techniques for raising and purifying antibodies are well known in the art and any such techniques may be chosen to achieve the preparations claimed in this invention. In a preferred embodiment of the invention, antibodies will immunoprecipitate APAF1 proteins or fragments of the APAF1 protein from solution as well as react with APAF1 peptides on Western or immunoblots of polyacrylamide gels. In another preferred embodiment, antibodies will detect APAF1 proteins and protein fragments in paraffin or frozen tissue sections, using immunocytochemical techniques.

Preferred embodiments relating to methods for detecting APAF1 (or mutants thereof) include enzyme linked immunosorbent assays (ELISA), radioimmunoassays (RIA), immunoradiometric assays (IRMA) and immunoenzymatic assays (IEMA), including sandwich assays using monoclonal and/or polyclonal antibodies. Exemplary sandwich assays are described by David et al. in U.S. Pat. Nos. 4,376,110 and 4,486,530, hereby incorporated by reference.

Methods of Use: Drug Screening

Polypeptides of the invention also may be used to assess the binding of small molecule substrates and ligands in, for example, cells, cell-free preparations, chemical libraries, and natural product mixtures. These substrates and ligands may be natural substrates and ligands or may be structural or functional mimetics. See, e.g., Coligan et al., Current Protocols in Immunology 1(2):Chapter 5 (1991). Thus, the invention also provides a method of screening compounds to identify those which enhance (agonist) or block (antagonist) the action of APAF1 polypeptides or polynucleotides, particularly those compounds for treating or preventing depression.

This invention is particularly useful for screening compounds by using a wild-type or mutant APAF1 polypeptide or a binding fragment thereof in any of a variety of drug screening techniques. The individual components of the assays described herein are available commercially and/or can be produced by an ordinary skilled artisan. APAF1 is described in U.S. Pat. No. 6,346,607 to Wang, issued Feb. 12, 2002, which is herein incorporated by reference in its entirety. The screens of the invention are intended to encompass the use of APAF1 homologs and APAF1 interacting proteins from any organism including, C. elegans and Drosphila, as well as human. The skilled artisan is capable of recognizing and employing APAF1 homologs and homologs of APAF1 interacting partners from other organisms in the assays of the invention. Drug screening can be performed as described herein or using well known techniques, such as described in U.S. Pat. Nos. 5,800,998 and 5,891,628, each incorporated herein by reference. Preferably test compounds that disrupt APAF1 bioactivity are tested in a secondary assay such as an animal depression model, a cellular based apoptosis assay, and transgenic animal models being homozygous or heterozygous for an APAF1 mutation that is associated with depression. Furthermore, as the skilled artisan readily understands, the screening assays described herein can be performed in a variety of configurations based on known APAF1 biochemistry, including, but not limited to testing to disrupt of inhibit apoptosome formation, inhibiting binding of ATP, dATP or an appropriate analog thereof from binding APAF1 and facilitating apoptosome formation, disruption or inhibition of cytochrome c binding to APAF1, enhancement of the WD40 repeates of APAF1 to autoinhibit the formation of apoptosome formation, and inhibition or disruption of pro-caspase-9 binding to the CARD (caspase recruitment domain) of APAF1. The assays can readily be configured to use a full apoptosome reconstitution assay or they can be based on inhibiting, e.g., protein:protein interactions, between members of the apoptosome using fragments of the proteins or full length proteins where appropriate. A preferred drug screen involves the use of an apoptosome reconstitution assay as described herein to identify compounds that inhibit or reduce caspase activation. A few representative embodiments are described below.

The APAF1 polypeptide or fragment employed in such a test can either be free in solution, affixed to a solid support, or borne on a cell surface. One method of drug screening utilizes eukaryotic or prokaryotic host cells which are stably transformed with recombinant polynucleotides expressing the polypeptide or fragment, preferably in competitive binding assays. Such cells, either in viable or fixed form, can be used for standard binding assays. One may measure, for example, for the formation of complexes between an APAF1 polypeptide or fragment and the agent being tested, or examine the degree to which the formation of a complex between an APAF1 polypeptide or fragment and a known ligand, e.g. APAF1 receptor (AT1), is interfered with by the agent being tested.

Thus, the present invention provides methods of screening for drugs comprising contacting such an agent with an APAF1 polypeptide or fragment thereof and assaying (i) for the presence of a complex between the agent and the APAF1 polypeptide or fragment, or (ii) for the presence of a complex between the APAF1 polypeptide or fragment and a ligand, by methods well known in the art. In such competitive binding assays the APAF1 polypeptide or fragment is typically labeled. Free APAF1 polypeptide or fragment is separated from that present in a protein:protein complex, and the amount of free (i.e., uncomplexed) label is a measure of the binding of the agent being tested to APAF1 or its interference with APAF1: ligand binding, respectively.

Another technique for drug screening provides high throughput screening for compounds having suitable binding affinity to the APAF1 polypeptides and is described in detail in Geysen, PCT published application WO 84/03564, published on Sep. 13, 1984. Briefly stated, large numbers of different small peptide test compounds are synthesized on a solid substrate, such as plastic pins or some other surface. The peptide test compounds are reacted with APAF1 polypeptides and washed. Bound APAF1 polypeptides are then detected by methods well known in the art.

Purified APAF1 can be coated directly onto plates for use in the aforementioned drug screening techniques. However, non-neutralizing antibodies to the polypeptide can be used to capture antibodies to immobilize the APAF1 polypeptide on the solid phase.

This invention also contemplates the use of competitive drug screening assays in which neutralizing antibodies capable of specifically binding the APAF1 polypeptide compete with a test compound for binding to the APAF1 polypeptide or fragments thereof. In this manner, the antibodies can be used to detect the presence of any peptide which shares one or more antigenic determinants of the APAF1 polypeptide.

A further technique for drug screening involves the use of host eukaryotic cell lines or cells (such as described above) which express a wild-type or mutant APAF1 gene and as a consequence of expression of wild type or mutant APAF1 demonstrate a specific phenotype. The phenotype of the cells is examined to determine if the compound is capable of modulating the phenotype and thereby APAF1 function.

Briefly, a method of screening for a substance which modulates activity of a polypeptide may include contacting one or more test substances with the polypeptide in a suitable reaction medium, testing the activity of the treated polypeptide and comparing that activity with the activity of the polypeptide in comparable reaction medium untreated with the test substance or substances. A difference in activity between the treated and untreated polypeptides is indicative of a modulating effect of the relevant test substance or substances.

Prior to or as well as being screened for modulation of activity, test substances may be screened for ability to interact with the polypeptide, e.g., in a yeast two-hybrid system (e.g., Bartel, P. L., et al. (1993) In: Cellular Interactions in Development: A Practical Approach, Oxford University Press, pp. 153 179; Fields, S, and Song, O-K. (1989) Nature 340:245 246; Chevray, P. M. and Nathans, D. N. (1992) Proc. Natl. Acad. Sci. USA 89:5789 5793; Lee, J. E., et al. (1995) Science 268:836 844). This system can be used as a coarse screen prior to testing a substance for actual ability to modulate activity of the polypeptide. Alternatively, the screen could be used to screen test substances for binding to an APAF1 specific binding partner, or to find mimetics of an APAF1 polypeptide.

In another embodiment, the invention provides methods of screening inhibitors of APAF1 activity or an altered APAF1 activity. In one aspect of this embodiment, the assays are configured to identify compounds that inhibit the ability of APAF1 to activate apoptosis. The ability of APAF1 to activate apoptosis can be determined by, e.g., analyzing the ability of APAF1 to activate caspase-9 or other caspases involved in activating apoptosis. The APAF1 based screening can employ wild-type APAF1 protein or, preferably mutant APAF1 proteins as disclosed herein.

The invention provides screening assays for identifying inhibitors that disrupt the interaction between APAF1, particularly an altered (mutant) APAF1, and its interacting partners such as APAF1, AT1, caspases (e.g., pro-caspase-9 and caspase-9), and/or cytochrome c. According to this embodiment, the screening methods are configured for selecting modulators of a protein complex formed between APAF1 or a homologue, derivative, altered (mutant) form, or fragment thereof and at least one protein with which it interacts to (or a homologue, derivative, altered form, or fragment thereof). In a preferred aspect of this embodiment, the screening assays are configured to identify compounds that modulate an interaction between an altered APAF1 and at least one protein with which it interacts to activate apoptosis. For example, in a specific aspect, a screen can involve using an APAF1-cytochrome c multimeric apoptosome complex based assay to examine the affect of test compounds to modulate procaspase-9 activation (Zou et al. (1999) J. Biol. Chem. 274: 11549 11556). More specifically, this screening assay involves contacting a test compound with a solution comprising, APAF1 (or an altered APAF1), cytochrome c, ATP or dATP, and procaspase-9, all of which are readily available to the skilled artisan. After incubation for an appropriate amount of time, the solution can be analyzed for the formation of caspase-9 from procaspase-9 using known techniques, or alternative the assay can also include procaspase-3, and the assay can be analyzed for the formation of caspase-3 from procaspase-3 using known techniques (caspase-3 activity assays). Accordingly, the screen can use complexes comprising wild-type APAF1 or altered APAF1, to examine the effect of test compounds on procaspase-9 (or procaspase-3) activation. Comparing the results between the wild-type APAF1 assays and the assays having an altered APAF1 can allow for the identification of drug candidates that selectively modulate altered APAF1 and/or its activation of the caspase cascade. Screening methods are also provided for selecting modulators of APAF1. The compounds identified in the screening methods of the present invention can be used in preventing or ameliorating depression and related disorders.

Thus, test compounds can be screened in an in vitro binding assay to identify compounds capable of binding or affecting a protein-protein interaction between APAF1 (including homologues, derivatives, altered (mutant) forms or fragments thereof) and proteins with which it interacts, such as APAF1, an APAF1 receptor (AT1), procaspase-9, caspase-9, and/or cytochrome c (including homologues, derivatives, altered (mutant) forms, or fragments thereof). In addition, in vitro dissociation assays may also be employed to select compounds capable of dissociating or destabilizing the protein complexes comprising APAF1 (or mutant APAF1) identified in accordance with the present invention. An in vitro screening assay can also be used to identify compounds that trigger or initiate the formation of, or stabilize, a protein complex of the present invention. In preferred embodiments, in vivo assays such as yeast two-hybrid assays and various derivatives thereof, preferably reverse two-hybrid assays, are utilized in identifying compounds that interfere with or disrupt protein-protein interactions between APAF1 or a homologue, derivative, altered form, mutant, or fragment thereof and an interacting partner which it interacts with such as APAF1, an APAF1 receptor (AT1), procaspase-9, caspase-9, and/or cytochrome c (or a homologue, derivative, altered form, mutant, or fragment thereof). In addition, systems such as yeast two-hybrid assays are also useful in selecting compounds capable of triggering or initiating, enhancing or stabilizing protein-protein interactions between APAF1 or a homologue, derivative, altered form, mutant, or fragment thereof and a protein with which it interacts, such as an APAF1, APAF1 receptor (AT1), procaspase-9, caspase-9, or cytochrome c (or a homologue, derivative, altered form, mutant, or fragment thereof). For example, the assays can entail (1) contacting the interacting members of the protein complex with each other in the presence of a test compound; and (2) detecting the interaction between the interacting members.

The test compounds may be screened in an in vitro assay to identify compounds capable of binding the protein complexes or interacting protein members thereof in accordance with the present invention. For this purpose, a test compound is contacted with a protein complex or an interacting protein member thereof under conditions and for a time sufficient to allow specific interaction between the test compound and the target components to occur, thereby resulting in the binding of the compound to the target, and the formation of a complex. Subsequently, the binding event is detected. Various screening techniques known in the art may be used in the present invention. The protein complexes and the interacting protein members thereof may be prepared by any suitable methods, e.g., by recombinant expression and purification. The protein complexes and/or interacting protein members thereof (both are referred to as "target" hereinafter in this section) may be free in solution. A test compound may be mixed with a target forming a liquid mixture. The compound may be labeled with a detectable marker. Upon mixing under suitable conditions, the binding complex having the compound and the target can be co-immunoprecipitated and washed. The compound in the precipitated complex can be detected based on the marker on the compound.

In a preferred embodiment, the target is immobilized on a solid support or on a cell surface. Preferably, the target can be arrayed into a protein microchip according to methods well-known in the art. For example, a target may be immobilized directly onto a microchip substrate such as glass slides or onto multi-well plates using non-neutralizing antibodies, i.e., antibodies capable of binding to the target but do not substantially affect its biological activities. To affect the screening, test compounds can be contacted with the immobilized target to allow binding to occur to form complexes under standard binding assay conditions. Either the targets or test compounds are labeled with a detectable marker using well-known labeling techniques. For example, U.S. Pat. No. 5,741,713 discloses combinatorial libraries of biochemical compounds labeled with NMR active isotopes. To identify binding compounds, one may measure the formation of the target-test compound complexes or kinetics for the formation thereof. When combinatorial libraries of organic non-peptide non-nucleic acid compounds are screened, it is preferred that labeled or encoded (or "tagged") combinatorial libraries are used to allow rapid decoding of lead structures. This is especially important because, unlike biological libraries, individual compounds found in chemical libraries cannot be amplified by self-amplification. Tagged combinatorial libraries are provided in, e.g., Borchardt and Still, J. Am. Chem. Soc., 116:373 374 (1994) and Moran et al., J. Am. Chem. Soc., 117:10787 10788 (1995), both of which are incorporated herein by reference.

Alternatively, the test compounds can be immobilized on a solid support, e.g. forming a microarray of test compounds. The target protein or protein complex is then contacted with the test compounds. The target can be labeled with any suitable detection marker. For example, the target can be labeled with radioactive isotopes or fluorescence marker before binding reaction occurs. Alternatively, after the binding reactions, antibodies that are immunoreactive with the target and are labeled with radioactive materials, fluorescence markers, enzymes, or labeled secondary anti-Ig antibodies can be used to detect any bound target thus identifying the binding compound. One example of this embodiment is the protein probing method. That is, the target provided in accordance with the present invention is used as a probe to screen expression libraries of proteins or random peptides. The expression libraries can be phage display libraries, in vitro translation-based libraries, or ordinary expression cDNA libraries. The libraries may be immobilized on a solid support such as nitrocellulose filters. See e.g., Sikela and Hahn, Proc. Natl. Acad. Sci. USA, 84:3038 3042 (1987). The probe can be labeled with a radioactive isotope or a fluorescence marker. Alternatively, the probe can be biotinylated and detected with a streptavidin-alkaline phosphatase conjugate. More conveniently, the bound probe can be detected with an antibody.

In yet another embodiment, a known ligand capable of binding to the target can be used in competitive binding assays. Complexes between the known ligand and the target can be formed and then contacted with test compounds. The ability of a test compound to interfere with the interaction between the target and the known ligand is measured. One exemplary ligand is an antibody capable of specifically binding the target. Particularly, such an antibody is especially useful for identifying peptides that share one or more antigenic determinants of the target protein complex or interacting protein members thereof.

In a specific embodiment, a protein complex used in the screening assay includes a hybrid protein which is formed by fusion of two interacting protein members or fragments or interaction domains thereof. The hybrid protein can also be designed such that it contains a detectable epitope tag fused thereto. Suitable examples of such epitope tags include sequences derived from, e.g., influenza virus hemagglutinin (HA), Simian Virus 5 (V5), polyhistidine (6×His), c-myc, lacZ, GST, and the like.

Test compounds may also be screened in in vitro assays to identify compounds capable of dissociating the protein complexes identified in accordance with the present invention. Thus, for example, dissociation of a protein complex comprising APAF1 (or mutant APAF1) and at least one interacting partner (such as APAF1, AT1, procaspase-9, caspase-9, and/or cytochrome c) following treatment with a test compound can be detected. Conversely, test compounds may also be screened to identify compounds capable of enhancing the interaction between APAF1 (or altered APAF1) and at least one interacting partner (such as AT1, procaspase-9, caspase-9, and/or cytochrome c) or stabilizing the protein complex formed by the proteins.

The assay can be conducted in similar manners as the binding assays described above. For example, the presence or absence of a particular protein complex can be detected by an antibody selectively immunoreactive with the protein complex. Thus, after incubation of the protein complex with a test compound, an immunoprecipitation assay can be conducted with the antibody. If the test compound disrupts the protein complex, then the amount of immunoprecipitated protein complex in this assay will be significantly less than that in a control assay in which the same protein complex is not contacted with the test compound. Similarly, two proteins the interaction between which is to be enhanced can be incubated together with a test compound. Thereafter, a protein complex can be detected by the selectively immunoreactive antibody. The amount of protein complex can be compared to that formed in the absence of the test compound. Various other detection methods can be suitable in the dissociation assay, as will be apparent to a skilled artisan apprised of the present disclosure.

Protein complexes comprising APAF1 (or mutant APAF1) and an interacting partner including APAF1, an APAF1 receptor (AT1), procaspase-9, caspase-9 and/or cytochrome c, can be used in screening assays to identify modulators of protein complexes comprising APAF1. In addition, mutants, homologues, derivatives or fragments of APAF1 and protein complexes containing such homologues, derivatives, mutants, or fragments may also be used in such screening assays. As used herein, the term "modulator" encompasses any compounds that can cause any form of alteration of the biological activities or functions of the proteins or protein complexes, including, e.g., enhancing or reducing their biological activities, increasing or decreasing their stability, altering their affinity or specificity to certain other biological molecules, etc. In addition, the term "modulator" as used herein also includes any compounds that simply bind APAF1, mutant APAF1, and/or the proteins complexes of the present invention. For example, a modulator can be an "interaction antagonist" capable of interfering with or disrupting or dissociating protein-protein interaction between APAF1 or a homologue, fragment or derivative thereof. A modulator can also be an "interaction agonist" that initiates or strengthens the interaction between the protein members of the protein complex of the present invention, or homologues, fragments, mutants, or derivatives thereof.

Accordingly, the present invention provides screening methods for selecting modulators of APAF1 or an altered form thereof, or protein complexes formed between an APAF1 receptor (AT1), procaspase-9, caspase-9, and/or cytochrome c or a mutant form thereof. The protein complex targets suitable in the screening assays of the present invention can be any embodiments of the protein complexes of the present invention. Preferably, protein fragments are used in forming the protein complexes. In specific embodiments, fusion proteins are used in which a detectable epitope tag is fused to an interacting protein or a homologue or derivative or fragment thereof. Suitable examples of such epitope tags include sequences derived from, e.g., influenza virus hemagglutinin (HA), Simian Virus 5 (V5), polyhistidine (6×His), c-myc, lacZ, GST, and the like. In addition, an interacting protein alone or a homologue or derivative or fragment thereof can also be used as a protein target in screening assays. Preferably, a detectable epitope tag is fused to the protein target. For example, compounds capable of binding to APAF1 protein, a homologue, derivative, mutant, or fragment thereof selected by the screening assays can be tested for their ability to inhibit or interfere with the interactions between APAF1 and APAF1, an APAF1 receptor (AT1), APAF1, procaspase-9, caspase-9, and/or cytochrome c.

The modulators selected in accordance with the screening methods of the present invention can be effective in modulating the functions or activities of APAF1 alone, or the protein complexes comprising APAF1 or mutant APAF1. Such complexes can include an APAF1 receptor (AT1), APAF1, procaspase-9, caspase-9, and/or cytochrome c. For example, compounds capable of binding the protein complexes can be capable of modulating the functions of the protein complexes. Additionally, compounds that interfere with, weaken, dissociate or disrupt, or alternatively, initiate, facilitate or stabilize the protein-protein interaction between the interacting protein members of the protein complexes can also be effective in modulating the functions or activities of the protein complexes. Thus, the compounds identified in the screening methods of the present invention can be made into therapeutically or prophylactically effective drugs for preventing or ameliorating diseases, disorders or symptoms caused by or associated with protein complexes comprising APAF1 (or mutant APAF1) and APAF1 (or mutant APAF) an APAF1 receptor (AT1), procaspase-9, caspase-9, and/or cytochrome c, or APAF1 separately. Alternatively, they can be used as leads to aid the design and identification of therapeutically or prophylactically effective compounds for diseases, disorders or symptoms caused by or associated with protein complexes comprising APAF1 (or an mutant APAF1) and APAF1 (or an mutant APAF1), an APAF1 receptor (AT1), procaspase-9, caspase-9, and/or cytochrome c, or APAF1 separately. The protein complexes and/or interacting protein members thereof in accordance with the present invention can be used in any of a variety of drug screening techniques. Drug screening can be performed as described herein or using well-known techniques, such as those described in U.S. Pat. Nos. 5,800,998 and 5,891,628, both of which are incorporated herein by reference.

In addition, potentially useful agents also include incomplete proteins, i.e., fragments of the interacting protein members that are capable of binding to their respective binding partners in a protein complex but are defective with respect to their normal cellular functions. For example, binding domains of the interacting member proteins of a protein complex can be used as competitive inhibitors of the activities of the protein complex. As will be apparent to skilled artisans, derivatives, homologues, or mutants of the binding domains can also be used. Binding domains can be easily identified using molecular biology techniques, e.g., mutagenesis in combination with yeast two-hybrid assays. Preferably, the protein fragment used is a fragment of an interacting protein member having a length of less than 90%, 80%, more preferably less than 75%, 65%, 50%, or less than 40% of the full length of the protein member. In one embodiment, an APAF1 receptor (AT1), procaspase-9, caspase-9, or cytochrome c protein fragment is administered. In a specific embodiment, one or more of the interaction domains of an APAF1 receptor (AT1), procaspase-9, caspase-9, or cytochrome c are administered to cells or tissue in vitro, or are administered to a patient in need of such treatment. For example, suitable protein fragments can include polypeptides having a contiguous span of 4, 5, 6, 7, 8, 9, 10, 11, 12, 13, 14, 15, 18, 20 or 25, preferably from 4 to 30, 40 or 50 amino acids or more of the sequence of an APAF1 receptor (AT1), procaspase-9, caspase-9, or cytochrome c that are capable of interacting with APAF1 or mutant APAF1. Also, suitable protein fragments can also include peptides capable of binding APAF1, or mutant APAF1, and having an amino acid sequence of from 4 to 30 amino acids that is at least 75%, 80%, 82%, 85%, 87%, 90%, 95% or more identical to a contiguous span of amino acids of an APAF1 receptor (AT1), procaspase-9, caspase-9, and/or cytochrome c of the same length. Alternatively, a polypeptide capable of interacting with an APAF1 receptor (AT1), procaspase-9, caspase-9, or cytochrome c and having a contiguous span of 4, 5, 6, 7, 8, 9, 10, 11, 12, 13, 14, 15, 18, 20 or 25, preferably from 4 to 30, 40 or 50 or more amino acids of the amino acid sequence of APAF1 can be administered. Also, other examples of suitable compounds include a peptide capable of binding an APAF1 receptor (AT1), procaspase-9, caspase-9, or cytochrome c and having an amino acid sequence of from 4 to 30, 40, 50 or more amino acids that is at least 75%, 80%, 82%, 85%, 87%, 90%, 95% or more identical to a contiguous span of amino acids of the same length from APAF1. In addition, the administered compounds can also be an antibody or antibody fragment, preferably single-chain antibody immunoreactive with APAF1 or an APAF1 receptor (AT1), procaspase-9, caspase-9, or cytochrome c or a protein complex of the present invention.

The protein fragments suitable as competitive inhibitors can be delivered into cells by direct cell internalization, receptor mediated endocytosis, or via a "transporter." It is noted that when the target proteins or protein complexes to be modulated reside inside cells, the compound administered to cells in vitro or in vivo in the method of the present invention preferably is delivered into the cells in order to achieve optimal results. Thus, preferably, the compound to be delivered is associated with a transporter capable of increasing the uptake of the compound by cells harboring the target protein or protein complex. As used herein, the term "transporter" refers to an entity (e.g., a compound or a composition or a physical structure formed from multiple copies of a compound or multiple different compounds) that is capable of facilitating the uptake of a compound of the present invention by animal cells, particularly human cells. Typically, the cell uptake of a compound of the present invention in the presence of a "transporter" is at least 20% higher, preferably at least 40%, 50%, 75%, and more preferably at least 100% higher than the cell uptake of the compound in the absence of the "transporter." Many molecules and structures known in the art can be used as "transporters." In one embodiment, a penetratin is used as a transporter. For example, the homeodomain of Antennapedia, a *Drosophila* transcription factor, can be used as a transporter to deliver a compound of the present invention. Indeed, any suitable member of the penetratin class of peptides can be used to carry a compound of the present invention into cells. Penetratins are disclosed in, e.g., Derossi et al., Trends Cell Biol., 8:84 87 (1998), which is incorporated herein by reference. Penetratins transport molecules attached thereto across cytoplasmic membranes or nuclear membranes efficiently, in a receptor-independent, energy-independent, and cell type-independent manner. Methods for using a penetratin as a carrier to deliver oligonucleotides and polypeptides are also disclosed in U.S. Pat. No. 6,080,724; Pooga et al., Nat. Biotech., 16:857 (1998); and Schutze et al., J. Immunol., 157:650 (1996), all of which are incorporated herein by reference. U.S. Pat. No. 6,080,724 defines the minimal requirements for a penetratin peptide as a peptide of 16 amino acids with 6 to 10 of which being hydrophobic. The amino acid at position 6 counting from either the N- or C-terminus is tryptophan, while the amino acids at positions 3 and 5 counting from either the N- or C-terminus are not both valine. Preferably, the helix 3 of the homeodomain of *Drosophila* Antennapedia is used as a transporter. More preferably, a peptide having a sequence of amino acid residues 43 58 of the homeodomain Antp is employed as a transporter. In addition, other naturally occurring homologs of the helix 3 of the homeodomain of *Drosophila* Antennapedia can be used. For example, homeodomains of Fushi-tarazu and Engrailed have been shown to be capable of transporting peptides into cells. See Han et al., Mol. Cells, 10:728 32 (2000). As used herein, the term "penetratin" also encompasses peptoid analogs of the penetratin peptides. Typically, the penetratin peptides and peptoid analogs thereof are covalently linked to a compound to be delivered into cells thus increasing the cellular uptake of the compound.

In another embodiment, the HIV-1 tat protein or a derivative thereof is used as a "transporter" covalently linked to a compound according to the present invention. The use of HIV-1 tat protein and derivatives thereof to deliver macromolecules into cells has been known in the art. See Green and Loewenstein, Cell, 55:1179 (1988); Frankel and Pabo, Cell, 55:1189 (1988); Vives et al., J. Biol. Chem., 272:16010 16017 (1997); Schwarze et al., Science, 285:1569 1572 (1999). It is known that the sequence responsible for cellular uptake consists of the highly basic region, amino acid residues 49 57. See e.g., Vives et al., J. Biol. Chem., 272:16010 16017 (1997); Wender et al., Proc. Nat'l Acad. Sci. USA, 97:13003 13008 (2000). The basic domain is believed to target the lipid bilayer component of cell membranes. It causes a covalently linked protein or nucleic acid to cross cell membrane rapidly in a cell type-independent manner. Proteins ranging in size from 15 to 120 kD have been delivered with this technology into a variety of cell types both in vitro and in vivo. See Schwarze et al., Science, 285:1569 1572 (1999). Any HIV tat-derived peptides or peptoid analogs thereof capable of transporting macromolecules such as peptides can be used for purposes of the present invention. For example, any native tat peptides having the highly basic region, amino acid residues 49 57 can be used as a transporter by covalently linking it to the compound to be delivered. In addition, various analogs of the tat peptide of amino acid residues 49 57 can also be useful transporters for purposes of this invention. Examples of various such analogs are disclosed in Wender et al., Proc. Nat'l Acad. Sci. USA, 97:13003 13008 (2000) (which is incorporated herein by reference) including, e.g., d-Tat$_{49-57}$, retro-inverso isomers of l- or d-Tat$_{49-57}$ (i.e., l-Tat$_{57-49}$ and d-Tat$_{57-49}$), L-arginine oligomers, D-arginine oligomers, L-lysine oligomers, D-lysine oligomers, L-histidine oligomers, D-histidine oligomers, L-ornithine oligomers, D-ornithine oligomers, and various homologues, derivatives (e.g., modified forms with conjugates linked to the small peptides) and peptoid analogs thereof.

Other useful transporters known in the art include, but are not limited to, short peptide sequences derived from fibroblast growth factor (See Lin et al., J. Biol. Chem., 270:14255 14258 (1998)), Galparan (See Pooga et al., FASEB J. 12:67 77 (1998)), and HSV-1 structural protein VP22 (See Elliott and O'Hare, Cell, 88:223 233 (1997)). As the above-described various transporters are generally peptides, fusion proteins can be conveniently made by recombinant expression to contain a transporter peptide covalently linked by a peptide bond to a competitive protein fragment. Alternatively, conventional methods can be used to chemically synthesize a transporter peptide or a peptide of the present invention or both.

The hybrid peptide can be administered to cells or tissue in vitro or to patients in a suitable pharmaceutical composition. In addition to peptide-based transporters, various other types of transporters can also be used, including but not limited to cationic liposomes (see Rui et al., J. Am. Chem. Soc., 120: 11213 11218 (1998)), dendrimers (Kono et al., Bioconjugate Chem., 10:1115 1121 (1999)), siderophores (Ghosh et al., Chem. Biol., 3:1011 1019 (1996)), etc. In a specific embodiment, the compound according to the present invention is encapsulated into liposomes for delivery into cells.

Additionally, when a compound according to the present invention is a peptide, it can be administered to cells by a gene therapy method. That is, a nucleic acid encoding the peptide can be administered to cells in vitro or to cells in a human or animal body. Any suitable gene therapy methods may be used for purposes of the present invention. Various gene therapy methods are well known in the art. Successes in gene therapy have been reported recently. See e.g., Kay et al., Nature Genet., 24:257 61 (2000); Cavazzana-Calvo et al., Science, 288:669 (2000); and Blaese et al., Science, 270: 475 (1995); Kantoff, et al., J. Exp. Med., 166:219 (1987).

Methods of Use: Rational Drug Design

The goal of rational drug design is to produce structural analogs of biologically active polypeptides of interest or of small molecules with which they interact (e.g., agonists, antagonists, inhibitors) in order to fashion drugs which are, for example, more active or stable forms of the polypeptide, or which, e.g., enhance or interfere with the function of a polypeptide in vivo. See, e.g., Hodgson, J. (1991) Bio/Technology 9:19 21. Rational drug design can be performed as described herein or using well known techniques, such as described in U.S. Pat. Nos. 5,800,998 and 5,891,628, each incorporated herein by reference.

In one approach, one first determines the three-dimensional structure of a protein of interest (e.g., APAF1 polypeptide, fragments of the APAF1 polypeptide, or apoptosome (Acehan et al. Mol. Cell. 9:423 432 (2002))) or, for example, of the APAF1-receptor or ligand complex, by x-ray crystallography, by computer modeling or most typically, by a combination of approaches. Less often, useful information regarding the structure of a polypeptide may be gained by modeling based on the structure of homologous proteins. An example of rational drug design is the development of HIV protease inhibitors (Erickson, J. et al., (1990) Science 249: 527 533). In addition, peptides (e.g., APAF1 polypeptide or fragments thereof) are analyzed by an alanine scan (Wells, J. A. (1991) Methods in Enzymol. 202:390 411). In this technique, an amino acid residue is replaced by Ala, and its effect on the peptide's activity is determined. Each of the amino acid residues of the peptide is analyzed in this manner to determine the important regions of the peptide.

It is also possible to isolate a target-specific antibody, selected by a functional assay, and then to solve its crystal structure. In principle, this approach yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced banks of peptides. Selected peptides would then act as the pharmacore. Thus, one may design drugs which have, e.g., improved APAF1 polypeptide activity or stability or which act as inhibitors, agonists, antagonists, etc. of APAF1 polypeptide activity.

Following identification of a substance which modulates or affects polypeptide activity, the substance can be investigated further. Furthermore, it can be manufactured and/or used in preparation, i.e., manufacture or formulation, or a composition such as a medicament, pharmaceutical composition or drug. These substances can be administered to individuals.

Thus, the present invention extends in various aspects not only to a substance identified using a nucleic acid molecule as a modulator of polypeptide activity, in accordance with what is disclosed herein, but also a pharmaceutical composition, medicament, drug or other composition comprising such a substance, a method comprising administration of such a composition comprising such a substance, a method comprising administration of such a composition to a patient, e.g., for treatment or prophylaxis of depression, use of such a substance in the manufacture of a composition for administration, e.g., for treatment or prophylaxis of depression, and a method of making a pharmaceutical composition comprising admixing such a substance with a pharmaceutically acceptable excipient, vehicle or carrier, and optionally other ingredients.

A substance identified as a modulator of polypeptide function can be peptide or non-peptide in nature. Non-peptide "small molecules" are often preferred for many in vivo pharmaceutical uses. Accordingly, a mimetic or mimic of the substance (particularly if a peptide) may be designed for pharmaceutical use.

The designing of mimetics to a known pharmaceutically active compound is a known approach to the development of pharmaceuticals based on a "lead" compound. This might be desirable where the active compound is difficult or expensive to synthesize or where it is unsuitable for a particular method of administration, e.g., pure peptides are unsuitable active agents for oral compositions as they tend to be quickly degraded by proteases in the alimentary canal. Mimetic design, synthesis and testing is generally used to avoid randomly screening large numbers of molecules for a target property.

There are several steps commonly taken in the design of a mimetic from a compound having a given target property. First, the particular parts of the compound that are critical and/or important in determining the target property are determined. In the case of a peptide, this can be done by systematically varying the amino acid residues in the peptide, e.g., by substituting each residue in turn. Alanine scans of peptide are commonly used to refine such peptide motifs. These parts or residues constituting the active region of the compound are known as its "pharmacophore".

Once the pharmacophore has been found, its structure is modeled according to its physical properties, e.g., stereochemistry, bonding, size and/or charge, using data from a range of sources, e.g., spectroscopic techniques, x-ray diffraction data and NMR. Computational analysis, similarity mapping (which models the charge and/or volume of a pharmacophore, rather than the bonding between atoms) and other techniques can be used in this modeling process.

In a variant of this approach, the three-dimensional structure of the ligand and its binding partner are modeled. This can be especially useful where the ligand and/or binding partner change conformation on binding, allowing the model to take account of this in the design of the mimetic.

A template molecule is then selected onto which chemical groups which mimic the pharmacophore can be grafted. The template molecule and the chemical groups grafted onto it can conveniently be selected so that the mimetic is easy to synthesize, is likely to be pharmacologically acceptable, and does not degrade in vivo, while retaining the biological activity of the lead compound. Alternatively, where the mimetic is peptide-based, further stability can be achieved by cyclizing the peptide, increasing its rigidity. The mimetic or mimetics found by this approach can then be screened to see whether they have the target property, or to what extent they exhibit it. Further optimization or modification can then be carried out to arrive at one or more final mimetics for in vivo or clinical testing.

Methods of Use: Nucleic Acid Based Therapies

According to the present invention, a method is also provided of supplying wild-type APAF1 function to a cell which carries mutant APAF1 alleles. The wild-type APAF1 gene or a part of the gene can be introduced into the cell in a vector such that the gene remains extrachromosomal. In such a situation, the gene will be expressed by the cell from the extrachromosomal location. If a gene fragment is introduced and expressed in a cell carrying a mutant APAF1 allele, the gene fragment should encode a part of the APAF1 protein which is required for normal physiological processes of the cell. More preferred is the situation where the wild-type APAF1 gene or a part thereof is introduced into the mutant cell in such a way that it recombines with the endogenous mutant APAF1 gene present in the cell. Such recombination requires a double recombination event which results in the correction of the APAF1 gene mutation. Vectors for introduction of genes both for recombination and for extrachromosomal maintenance are known in the art, and any suitable vector may be used. Methods for introducing DNA into cells such as electroporation, calcium phosphate coprecipitation and viral transduction are known in the art, and the choice of method is within the competence of the routineer. See also U.S. Pat. Nos. 5,800,998 and 5,891,628, each incorporated by reference herein.

Among the compounds which may exhibit anti-depression activity are antisense, siRNA, ribozyme, and triple helix molecules. Such molecules may be designed to reduce or inhibit mutant APAF1 activity. Techniques for the production and use of such molecules are well known to those of skill in the art, such as described herein or in U.S. Pat. No. 5,800,998, incorporated herein by reference.

Antisense RNA and DNA molecules act to directly block the translation of mRNA by binding to targeted mRNA and preventing protein translation. With respect to antisense DNA, oligodeoxyribonucleotides derived from the translation initiation site, e.g., between the −10 and +10 regions of the APAF1 nucleotide sequence of interest, are preferred.

In one embodiment, the inhibitors of cellular levels of APAF1 are double-stranded small interfering RNA (siRNA) compounds or a modified equivalent thereof. APAF1 siRNA are commercially available (target sequence=SEQ ID NO:45'-AAT TGG TGC ACT TTT ACG TGA-3') from, for example, Dharmacon (Lafayette, Colo.) (citing Lassus et al. Science 297:1352 1354 (2002)). Alternatively, the skilled artisan, apprised of this disclosure, is capable of providing siRNA useful for reducing the levels of APAF1 protein (or mutants thereof).

As is generally known in the art, siRNA compounds are RNA duplexes comprising two complementary single-stranded RNAs of 21 nucleotides that form 19 base pairs and possess 3' overhangs of two nucleotides. See Elbashir et al., Nature 411:494 498 (2001); and PCT Publication Nos. WO 00/44895; WO 01/36646; WO 99/32619; WO 00/01846; WO 01/29058; WO 99/07409; and WO 00/44914. When appropriately targeted via its nucleotide sequence to a specific mRNA in cells, a siRNA can specifically suppress gene expression through a process known as RNA interference (RNAi). See e.g., Zamore & Aronin, Nature Medicine, 9:266 267 (2003). siRNAs can reduce the cellular level of specific mRNAs, and decrease the level of proteins coded by such mRNAs. siRNAs utilize sequence complementarity to target an mRNA for destruction, and are sequence-specific. Thus, they can be highly target-specific, and in mammals have been shown to target mRNAs encoded by different alleles of the same gene. Because of this precision, side effects typically associated with traditional drugs can be reduced or eliminated. In addition, they are relatively stable, and like antisense and ribozyme molecules, they can also be modified to achieve improved pharmaceutical characteristics, such as increased stability, deliverability, and ease of manufacture. Moreover, because siRNA molecules take advantage of a natural cellular pathway, i.e., RNA interference, they are highly efficient in destroying targeted mRNA molecules. As a result, it is relatively easy to achieve a therapeutically effective concentration of an siRNA compound in patients. Thus, siRNAs are a new class of drugs being actively developed by pharmaceutical companies.

In vivo inhibition of specific gene expression by RNAi was achieved in various organisms including mammals. For example, Song et al., Nature Medicine, 9:347 351 (2003) demonstrate that intravenous injection of Fas siRNA compounds into laboratory mice with autoimmune hepatitis specifically reduced Fas mRNA levels and expression of Fas protein in mouse liver cells. The gene silencing effect persisted without diminution for 10 days after the intravenous injection. The injected siRNA was effective in protecting the mice from liver failure and fibrosis. Song et al., Nature Medicine, 9:347 351 (2003). Several other approaches for delivery of siRNA into animals have also proved to be successful. See e.g., McCaffery et al., Nature, 418:38 39 (2002); Lewis et al., Nature Genetics, 32:107 108 (2002); and Xia et al., Nature Biotech., 20:1006 1010 (2002).

The siRNA compounds provided according to the present invention can be synthesized using conventional RNA synthesis methods. For example, they can be chemically synthesized using appropriately protected ribonucleoside phosphoramidites and a conventional DNA/RNA synthesizer. Various applicable methods for RNA synthesis are disclosed in, e.g., Usman et al., J. Am. Chem. Soc., 109:7845 7854 (1987) and Scaringe et al., Nucleic Acids Res., 18:5433 5441 (1990). Custom siRNA synthesis services are available from commercial vendors such as Ambion (Austin, Tex., USA), Dharmacon Research (Lafayette, Colo., USA), Pierce Chemical (Rockford, Ill., USA), ChemGenes (Ashland, Mass., USA), Proligo (Hamburg, Germany), and Cruachem (Glasgow, UK).

The siRNA compounds can also be various modified equivalents of the structures in of any APAF1 siRNA. As used herein, "modified equivalent" means a modified form of a particular siRNA compound having the same target-specificity (i.e., recognizing the same mRNA molecules that complement the unmodified particular siRNA compound). Thus, a modified equivalent of an unmodified siRNA compound can have modified ribonucleotides, that is, ribonucleotides that contain a modification in the chemical structure of an unmodified nucleotide base, sugar and/or phosphate (or phosphodiester linkage). As is known in the art, an "unmodified ribonucleotide" has one of the bases adenine, cytosine, guanine, and uracil joined to the 1' carbon of beta-D-ribo-furanose.

Preferably, modified siRNA compounds contain modified backbones or non-natural internucleoside linkages, e.g., modified phosphorous-containing backbones and non-phosphorous backbones such as morpholino backbones; siloxane, sulfide, sulfoxide, sulfone, sulfonate, sulfonamide, and sulfamate backbones; formacetyl and thioformacetyl backbones; alkene-containing backbones; methyleneimino and methylenehydrazino backbones; amide backbones, and the like.

Examples of modified phosphorous-containing backbones include, but are not limited to phosphorothioates, phosphorodithioates, chiral phosphorothioates, phosphotriesters, aminoalkylphosphotriesters, alkyl phosphonates, thionoalkylphosphonates, phosphinates, phosphoramidates, thionophosphoramidates, thionoalkylphosphotriesters, and boranophosphates and various salt forms thereof. See e.g., U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference.

Examples of the non-phosphorous containing backbones described above are disclosed in, e.g., U.S. Pat. Nos. 5,034,506; 5,185,444; 5,214,134; 5,216,141; 5,235,033; 5,264,562; 5,264,564; 5,405,938; 5,434,257; 5,470,967; 5,489,677; 5,541,307; 5,561,225; 5,596,086; 5,610,289; 5,602,240; 5,608,046; 5,610,289; 5,618,704; 5,623,070; 5,663,312; 5,677,437; and 5,677,439, each of which is herein incorporated by reference.

Modified forms of siRNA compounds can also contain modified nucleosides (nucleoside analogs), i.e., modified purine or pyrimidine bases, e.g., 5-substituted pyrimidines, 6-azapyrimidines, pyridin-4-one, pyridin-2-one, phenyl, pseudouracil, 2,4,6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine), 2-thiouridine, 4-thiouridine, 5(carboxyhydroxymethyl)uridine, 5'-carboxymethylaminomethyl-2-thiouridine, 5-carboxymethylaminomethyluridine, 5-methoxyaminomethyl-2-thiouridine, 5-methylaminomethyluridine, 5-methylcarbonylmethyluridine, 5-methyloxyuridine, 5-methyl-2-thiouridine, 4-acetylcytidine, 3-methylcytidine, propyne, quesosine, wybutosine, wybutoxosine, beta-D-galactosylqueosine, N-2, N-6 and O-substituted purines, inosine, 1-methyladenosine, 1-methylinosine, 2,2-dimethylguanosine, 2-methyladenosine, 2-methylguanosine, N6-methyladenosine, 7-methylguanosine, 2-methylthio-N-6-isopentenyladenosine, beta-D-mannosylqueosine, uridine-5-oxyacetic acid, 2-thiocytidine, threonine derivatives, and the like. See e.g., U.S. Pat. Nos. 3,687,808; 4,845,205; 5,130,302; 5,175,273; 5,367,066; 5,432,272; 5,459,255; 5,484,908; 5,502,177; 5,525,711; 5,587,469; 5,594,121; 5,596,091; 5,681,941; and 5,750,692, PCT Publication No. WO 92/07065; PCT Publication No. WO 93/15187; and Limbach et al., Nucleic Acids Res., 22:2183 (1994), each of which is incorporated herein by reference in its entirety.

In addition, modified siRNA compounds can also have substituted or modified sugar moieties, e.g., 2'-O-methoxyethyl sugar moieties. See e.g., U.S. Pat. Nos. 4,981,957; 5,118,800; 5,319,080; 5,393,878; 5,446,137; 5,466,786; 5,514,785; 5,567,811; 5,576,427; 5,591,722; 5,610,300; 5,627,0531 5,639,873; 5,646,265; 5,658,873; 5,670,633; and 5,700,920, each of which is herein incorporated by reference.

Modified siRNA compounds may be synthesized by the methods disclosed in, e.g., U.S. Pat. No. 5,652,094; International Publication Nos. WO 91/03162; WO 92/07065 and WO 93/15187; European Patent Application No. 92110298.4; Perrault et al., Nature, 344:565 (1990); Pieken et al., Science, 253:314 (1991); and Usman and Cedergren, Trends in Biochem. Sci., 17:334 (1992).

Preferably, the 3' overhangs of the siRNAs of the present invention are modified to provide resistance to cellular nucleases. In one embodiment the 3' overhangs comprise 2'-deoxyribonucleotides. In a preferred embodiment these 3' overhangs comprise a dinucleotide made of two 2'-deoxythymine residues (i.e., dTdT) linked by a 5'-3' phosphodiester linkage.

siRNA compounds may be administered to mammals by various methods through different routes. For example, they can be administered by intravenous injection. See Song et al., Nature Medicine, 9:347 351 (2003). They can also be delivered directly to a particular organ or tissue by any suitable localized administration methods. Several other approaches for delivery of siRNA into animals have also proved to be successful. See e.g., McCaffery et al., Nature, 418:38 39 (2002); Lewis et al., Nature Genetics, 32:107 108 (2002); and Xia et al., Nature Biotech., 20:1006 1010 (2002). Alternatively, they may be delivered encapsulated in liposomes, by iontophoresis, or by incorporation into other vehicles such as hydrogels, cyclodextrins, biodegradable nanocapsules, and bioadhesive microspheres.

In addition, they can also be delivered by a gene therapy approach, using a DNA vector from which siRNA compounds in, e.g., small hairpin form (shRNA), can be transcribed directly. Recent studies have demonstrated that while double-stranded siRNAs are very effective at mediating RNAi, short, single-stranded, hairpin-shaped RNAs can also mediate RNAi, presumably because they fold into intramolecular duplexes that are processed into double-stranded siRNAs by cellular enzymes. Sui et al., Proc. Natl. Acad. Sci. U.S.A., 99:5515 5520 (2002); Yu et al., Proc. Natl. Acad. Sci. U.S.A., 99:6047 6052 (2002); and Paul et al., Nature Biotech., 20:505 508 (2002)). This discovery has significant and far-reaching implications, since the production of such shRNAs can be readily achieved in vivo by transfecting cells or tissues with DNA vectors bearing short inverted repeats separated by a small number of (e.g., 3 to 9) nucleotides that direct the transcription of such small hairpin RNAs. Additionally, if mechanisms are included to direct the integration of the transcription cassette into the host cell genome, or to ensure the stability of the transcription vector, the RNAi caused by the encoded shRNAs, can be made stable and heritable. Not only have such techniques been used to "knock down" the expression of specific genes in mammalian cells, but they have now been successfully employed to knock down the expression of exogenously expressed transgenes, as well as endogenous genes in the brain and liver of living mice. See generally Hannon, Nature. 418:244 251 (2002) and Shi, Trends Genet., 19:9 12 (2003); see also Xia et al., Nature Biotech., 20:1006 1010 (2002).

Additional siRNA compounds targeted at different sites of the mRNA corresponding to APAF 1 can also be designed and synthesized according to general guidelines provided herein and generally known to skilled artisans. See e.g., Elbashir, et al. (Nature 411: 494 498 (2001). For example, guidelines have been compiled into "The siRNA User Guide" which is available at the following web address: www.mpibpc.gwdg.de/abteilungen/100/105/sima.html.

Additionally, to assist in the design of siRNAs for the efficient RNAi-mediated silencing of any target gene, several siRNA supply companies maintain web-based design tools that utilize these general guidelines for "picking" siRNAs when presented with the mRNA or coding DNA sequence of the target gene. Examples of such tools can be found at the web sites of Dharmacon, Inc. (Lafayette, Colo.), Ambion, Inc. (Austin, Tex.), an of approximately 30 50%; (3) lack of trinucleotide repeats, especially GGG and CCC, and (4) being unique to the target gene (i.e., sequences that share no significant homology with genes other than the one being targeted), so that other genes are not inadvertently targeted by the same siRNA designed for this particular target sequence. Another criterion to be considered is whether or not the target sequence includes a known polymorphic site. If so, siRNAs designed to target one particular allele may not effectively target another allele, since single base mismatches between the target sequence and its complementary strand in a given siRNA can greatly reduce the effectiveness of RNAi induced by that siRNA. Given that target sequence and such design tools and design criteria, an ordinarily skilled artisan apprised of the present disclosure should be able to design and synthesized additional siRNA compounds useful in reducing the mRNA level and therefore APAF1 protein level which can be used to treat depression according to the invention.

In another embodiment, the inhibitors of cellular levels of APAF1 are antisense compounds, or a modified equivalent thereof. U.S. Pat. No. 6,468,795, which is hereby incorporated by reference in its entirety, discloses APAF1 antisense compounds and methods of modulating APAF1. These antisense compounds and methods can be employed to treat and/or prevent depression according to the therapeutic methods of the invention. The antisense compounds according to this embodiment specifically inhibit the expression of APAF1. As is known in the art, antisense drugs generally act by hybridizing to a particular target nucleic acid thus blocking gene expression (particularly protein translation from mRNA). Methods for designing antisense compounds and using such compounds in treating diseases are well known and well developed in the art. For example, the antisense drug Vitravene® (fomivirsen), a 21-base long oligonucleotide, has been successfully developed and marketed by Isis Pharmaceuticals, Inc. for treating cytomegalovirus (CMV)-induced retinitis.

In addition to the antisense compounds provided in U.S. Pat. No. 6,468,795, other antisense compounds useful in inhibiting protein translation from the APAF1 mRNA can also be designed and prepared. Any methods for designing and making antisense compounds may be used for purpose of the present invention. See generally, Sanghvi et al., eds., Antisense Research and Applications, CRC Press, Boca Raton, 1993. Typically, antisense compounds are oligonucleotides designed based on the nucleotide sequence of the host cell's protein(s) involved in viral budding (or egress) mRNA or gene. In particular, antisense compounds can be designed to specifically hybridize to a particular region of the host cell's protein(s) involved in viral budding (or egress) genomic sequence or mRNA to interfere with replication, transcription, or translation. As used herein, the term "specifically hybridize" or variations thereof means a sufficient degree of complementarity or pairing between an antisense oligo and a target DNA or mRNA such that stable and specific binding occurs therebetween. In particular, 100% complementarity or pairing is desirable but not required. Specific hybridization occurs when sufficient hybridization occurs between the antisense compound and its intended target nucleic acids in the substantial absence of non-specific binding of the antisense compound to non-target sequences under predetermined conditions, e.g., for purposes of in vivo treatment, preferably under physiological conditions. Preferably, specific hybridization results in the interference with normal expression of the gene product encoded by the target DNA or mRNA.

For example, an antisense compound can be designed to specifically hybridize to the replication or transcription regulatory regions of a target gene, or the translation regulatory regions such as translation initiation region and exon/intron junctions, or the coding regions of a target mRNA.

As is generally known in the art, commonly used oligonucleotides are oligomers or polymers of ribonucleic acid or deoxyribonucleic acid having a combination of naturally-occurring purine and pyrimidine bases, sugars and covalent linkages between nucleosides including a phosphate group in a phosphodiester linkage. However, it is noted that the term "oligonucleotides" also encompasses various non-naturally occurring mimetics and derivatives, i.e., modified forms, of naturally-occurring oligonucleotides as described below. Typically an antisense compound of the present invention is an oligonucleotide having from about 6 to about 200, preferably from about 8 to about 30 nucleoside bases.

The antisense compounds preferably contain modified backbones or non-natural internucleoside linkages, including, but not limited to, modified phosphorous-containing backbones and non-phosphorous backbones such as morpholino backbones; siloxane, sulfide, sulfoxide, sulfone, sulfonate, sulfonamide, and sulfamate backbones; formacetyl and thioformacetyl backbones; alkene-containing backbones; methyleneimino and methylenehydrazino backbones; amide backbones, and the like.

Examples of modified phosphorous-containing backbones include, but are not limited to phosphorothioates, phosphorodithioates, chiral phosphorothioates, phosphotriesters, aminoalkylphosphotriesters, alkyl phosphonates, thionoalkylphosphonates, phosphinates, phosphoramidates, thionophosphoramidates, thionoalkylphosphotriesters, and boranophosphates and various salt forms thereof. See e.g., U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference.

Examples of the non-phosphorous containing backbones described above are disclosed in, e.g., U.S. Pat. Nos. 5,034,506; 5,185,444; 5,214,134; 5,216,141; 5,235,033; 5,264,562; 5,264,564; 5,405,938; 5,434,257; 5,470,967; 5,489,677; 5,541,307; 5,561,225; 5,596,086; 5,610,289; 5,602,240; 5,608,046; 5,610,289; 5,618,704; 5,623,070; 5,663,312; 5,677,437; and 5,677,439, each of which is herein incorporated by reference.

Another useful modified oligonucleotide is peptide nucleic acid (PNA), in which the sugar-phosphate backbone of an oligonucleotide is replaced with an amide containing backbone, e.g., an aminoethylglycine backbone. See U.S. Pat. Nos. 5,539,082 and 5,714,331; and Nielsen et al., Science, 254, 1497 1500 (1991), all of which are incorporated herein by reference. PNA antisense compounds are resistant to RNAse H digestion and thus exhibit longer half-lives within cells. In addition, various modifications may be made in PNA backbones to impart desirable drug profiles such as better stability, increased drug uptake, higher affinity to target nucleic acid, etc.

Alternatively, the antisense compounds are oligonucleotides containing modified nucleosides, i.e., modified purine or pyrimidine bases, e.g., 5-substituted pyrimidines, 6-azapyrimidines, and N-2, N-6 and O-substituted purines, and the like. See e.g., U.S. patent Nos. as well as U.S. Pat. Nos. 3,687,808; 4,845,205; 5,130,302; 5,175,273; 5,367,066; 5,432,272; 5,459,255; 5,484,908; 5,502,177; 5,525,711; 5,587,469; 5,594,121; 5,596,091; 5,681,941; and 5,750,692, each of which is herein incorporated by reference in its entirety.

In addition, oligonucleotides with substituted or modified sugar moieties may also be used. For example, an antisense compound may have one or more 2'-O-methoxyethyl sugar moieties. See e.g., U.S. Pat. Nos. 4,981,957; 5,118,800; 5,319,080; 5,393,878; 5,446,137; 5,466,786; 5,514,785; 5,567,811; 5,576,427; 5,591,722; 5,610,300; 5,627,0531 5,639,873; 5,646,265; 5,658,873; 5,670,633; and 5,700,920, each of which is herein incorporated by reference.

Other types of oligonucleotide modifications are also useful including linking an oligonucleotide to a lipid, phospholipid or cholesterol moiety, cholic acid, thioether, aliphatic chain, polyamine, polyethylene glycol (PEG), or a protein or peptide. The modified oligonucleotides may exhibit increased uptake into cells, and/or improved stability, i.e., resistance to nuclease digestion and other biodegradation. See e.g., U.S. Pat. No. 4,522,811; Burnham, Am. J. Hosp. Pharm., 15:210 218 (1994).

Antisense compounds can be synthesized using any suitable methods known in the art. In fact, antisense compounds may be custom made by commercial suppliers. Alternatively, antisense compounds may be prepared using DNA/RNA synthesizers commercially available from various vendors, e.g., Applied Biosystems Group of Norwalk, Conn.

The antisense compounds can be formulated into a pharmaceutical composition with suitable carriers and administered into a patient using any suitable route of administration. Alternatively, the antisense compounds may also be used in a "gene-therapy" approach. That is, the oligonucleotide is subcloned into a suitable vector and transformed into human cells. The antisense oligonucleotide is then produced in vivo through transcription.

Ribozymes are enzymatic RNA molecules capable of catalyzing the specific cleavage of RNA. The mechanism of ribozyme action involves sequence specific hybridization of the ribozyme molecule to complementary target RNA, followed by an endonucleolytic cleavage. The composition of ribozyme molecules must include one or more sequences complementary to the target APAF1 mRNA, preferably the mutant APAF1 mRNA, and must include the well known catalytic sequence responsible for mRNA cleavage. For this sequence, see U.S. Pat. No. 5,093,246, which is incorporated by reference herein in its entirety. As such, within the scope of the invention are engineered hammerhead motif ribozyme molecules that specifically and efficiently catalyze endonucleolytic cleavage of RNA sequences encoding APAF1, preferably mutant APAF1 proteins.

Specific ribozyme cleavage sites within any potential RNA target are initially identified by scanning the target molecule for ribozyme cleavage sites which include the following sequence: GUA, GUU and GUC. Once identified, short RNA sequences of between 15 and ribonucleotides corresponding to the region of the target gene containing the cleavage site may be evaluated for predicted structural features, such as secondary structure, that may render the oligonucleotide sequence unsuitable. The suitability of candidate targets may also be evaluated by testing their accessibility to hybridization with complementary oligonucleotides, using ribonuclease protection assays.

Nucleic acid molecules to be used in triplex helix formation should be single stranded and composed of deoxynucleotides. The base composition of these oligonucleotides must be designed to promote triple helix formation via Hoogsteen base pairing rules, which generally require sizeable stretches of either purines or pyrimidines to be present on one strand of a duplex. Nucleotide sequences may be pyrimidine-based, which will result in TAT and CGC$^+$ triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, containing a stretch of guanidine residues. These molecules will form a triple helix with a DNA duplex that is rich in GC pairs, in which the majority of the purine residues are located on a single strand of the targeted duplex, resulting in GGC triplets across the three strands in the triplex.

Alternatively, the potential sequences that can be targeted for triple helix formation may be increased by creating a so called "switchback" nucleic acid molecule. Switchback molecules are synthesized in an alternating 5'-3',3'-5' manner, such that they base pair with one strand of a duplex first and then the other, eliminating the necessity for a sizeable stretch of either purines or pyrimidines to be present on one strand of a duplex.

It is possible that the siRNA, antisense, ribozyme, and/or triple helix molecules described herein may reduce or inhibit the translation of mRNA produced by both normal and mutant APAF1 alleles. In order to ensure that substantial normal levels of APAF1 activity are maintained in the cell, nucleic acid molecules that encode and express APAF1 polypeptides exhibiting normal APAF1 activity can be introduced into cells which do not contain sequences susceptible to the siRNA, antisense, ribozyme, or triple helix treatments. Such sequences can be introduced via gene therapy methods. Alternatively, it may be preferable to co-administer normal APAF1 protein into the cell or tissue in order to maintain the requisite level of cellular or tissue APAF1 activity.

Antisense RNA and DNA molecules, siRNA molecules, ribozyme molecules, and triple helix molecules of the invention can be prepared by any method known in the art for the synthesis of DNA and RNA molecules. These include techniques for chemically synthesizing oligodeoxyribonucleotides and oligoribonucleotides well known in the art such as for example solid phase phosphoramidite chemical synthesis. Alternatively, RNA molecules can be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Various well-known modifications to the DNA molecules can be introduced as a means of increasing intracellular stability and half-life. Possible modifications include, but are not limited to, the addition of flanking sequences of ribo- or deoxy-nucleotides to the 5' and/or 3' ends of the molecule or the use of phosphorothioate or 2' O-methyl rather than phosphodiesterase linkages within the oligodeoxyribonucleotide backbone.

Gene therapy would be carried out according to generally accepted methods, for example, as described in further detail in U.S. Pat. Nos. 5,837,492 and 5,800,998 and references cited therein, all incorporated by reference herein. Expression vectors in the context of gene therapy are meant to include those constructs containing sequences sufficient to express a polynucleotide that has been cloned therein. In viral expression vectors, the construct contains viral sequences sufficient to support packaging of the construct. If the polynucleotide encodes an antisense polynucleotide or a ribozyme, expression will produce the antisense polynucleotide or ribozyme. Thus in this context, expression does not require that a protein product be synthesized. In addition to the polynucleotide cloned into the expression vector, the vector also contains a promoter functional in eukaryotic cells. The cloned polynucleotide sequence is under control of this promoter. Suitable eukaryotic promoters include those described above. The expression vector may also include sequences, such as selectable markers and other sequences conventionally used.

Methods of Use: Peptide Therapy

Peptides which have APAF1 activity can be supplied to cells which carry mutant or missing APAF1 alleles. Peptide therapy is performed as described herein or using well known techniques, such as described in U.S. Pat. Nos. 5,800,998 and 5,891,628, each incorporated herein by reference.

Protein can be produced by expression of the cDNA sequence in bacteria, for example, using known expression vectors. Alternatively, APAF1 polypeptide can be extracted from APAF1-producing mammalian cells. In addition, the techniques of synthetic chemistry can be employed to synthesize APAF1 protein. Any of such techniques can provide the preparation of the present invention which comprises the APAF1 protein. Preparation is substantially free of other human proteins. This is most readily accomplished by synthesis in a microorganism or in vitro.

Active APAF1 molecules can be introduced into cells by microinjection or by use of liposomes, for example. Alternatively, some active molecules can be taken up by cells, actively or by diffusion. Extracellular application of the APAF1 gene product can be sufficient to affect the development and or progression of depression. Supply of molecules with APAF1 activity should lead to partial reversal of the depression phenotype. Other molecules with APAF1 activity (for example, peptides, drugs or organic compounds) can also be used to effect such a reversal. Modified polypeptides having substantially similar function are also used for peptide therapy.

Alternatively, antibodies that are both specific for mutant APAF1 gene product and interfere with its activity can be used. Such antibodies can be generated using standard techniques described herein or using conventional techniques, such as described in U.S. Pat. Nos. 5,837,492; 5,800,998 and 5,891,628, against the proteins themselves or against peptides corresponding to the binding domains of the proteins. Such antibodies include, but are not limited to, polyclonal, monoclonal, Fab fragments, F(ab')$_2$ fragments, single chain antibodies, chimeric antibodies, humanized antibodies etc.

Methods of Use: Transformed Hosts; Transgenic/Knockout Animals and Models

Similarly, cells and animals which carry a mutant APAF1 allele can be used as model systems to study and test for substances which have potential as therapeutic agents. These can be isolated from individuals with APAF1 mutations, either somatic or germline. Alternatively, the cell line can be engineered to carry the mutation in the APAF1 allele, as described above. After a test substance is applied to the cells, the phenotype of the cell is determined. Any trait of the transformed cells can be assessed using techniques well known in the art. Transformed hosts, transgenic/knockout animals and models are prepared and used as described herein or using well known techniques, such as described in U.S. Pat. Nos. 5,800,998 and 5,891,628, each incorporated herein by reference.

Animals for testing therapeutic agents can be selected after mutagenesis of whole animals or after treatment of germline cells or zygotes. Such treatments include insertion of mutant APAF1 alleles, usually from a second animal species, as well as insertion of disrupted homologous genes. Alternatively, the endogenous APAF1 gene(s) of the animals can be disrupted by insertion or deletion mutation or other genetic alterations using conventional techniques (Capecchi, M. R. (1989) Science 244:1288; Valancius and Smithies, 1991; Hasty, P., K., et al. (1991) Nature 350:243; Shinkai, Y., et al. (1992) Cell 68:855; Mombaerts, P., et al. (1992) Cell 68:869; Philpott, K. L., et al. (1992) Science 256:1448; Snouwaert, J. N., et al. (1992) Science 257:1083; Donehower, L. A., et al. (1992) Nature 356:215) to produce knockout or transplacement animals. A transplacement is similar to a knockout because the endogenous gene is replaced, but in the case of a transplacement the replacement is by another version of the same gene. After test substances have been administered to the animals, the depression phenotype must be assessed. If the test substance prevents or suppresses the depression phenotype, then the test substance is a candidate therapeutic agent for the treatment of depression. These animal models provide an extremely important testing vehicle for potential therapeutic products.

In one embodiment of the invention, transgenic animals are produced which contain a functional transgene encoding a functional APAF1 polypeptide or variants thereof. Transgenic animals expressing APAF1 transgenes, recombinant cell lines derived from such animals and transgenic embryos may be useful in methods for screening for and identifying agents that induce or repress function of APAF1. Transgenic animals of the present invention also can be used as models for studying indications such as depression.

In one embodiment of the invention, an APAF1 transgene is introduced into a non-human host to produce a transgenic animal expressing a human, murine or other species APAF1 gene. The transgenic animal is produced by the integration of the transgene into the genome in a manner that permits the expression of the transgene. Methods for producing transgenic animals are generally described by Wagner and Hoppe (U.S. Pat. No. 4,873,191; which is incorporated herein by reference), Brinster et al. (1985) Mol. Cell. Biol. 8:1977 83; which is incorporated herein by reference in its entirety) and in "Manipulating the Mouse Embryo; A Laboratory Manual" 2nd edition (eds., Hogan, Beddington, Costantimi and Long, Cold Spring Harbor Laboratory Press, 1994; which is incorporated herein by reference in its entirety).

It can be desirable to replace the endogenous APAF1 by homologous recombination between the transgene or a mutant gene and the endogenous gene; or the endogenous gene may be eliminated by deletion as in the preparation of "knock-out" animals. Typically, an APAF1 gene flanked by genomic sequences is transferred by microinjection into a fertilized egg. The microinjected eggs are implanted into a host female, and the progeny are screened for the expression of the transgene. Transgenic animals can be produced from the fertilized eggs from a number of animals including, but not limited to reptiles, amphibians, birds, mammals, and fish. Within a particularly preferred embodiment, transgenic mice are generated which overexpress APAF1 or express a mutant form of the polypeptide. Alternatively, the absence of an APAF1 in "knock-out" mice permits the study of the effects that loss of APAF1 protein has on a cell in vivo. Knock-out mice also provide a model for the development of APAF 1-related depression.

Methods for producing knockout animals are generally described by Shastry (Shastry et al. (1995) Experientia 51:1028 1039; Shastry et al. (1998) Mol. Cell. Biochem. 181:163 179) and Osterrieder and Wolf (1998) Rev. Sci. Tech. 17:351 364. The production of conditional knockout animals, in which the gene is active until knocked out at the desired time is generally described by Feil et al., (1996) Proc. Natl. Acad. Sci. USA 93:10887 10890; Gagneten et al. (1997) Nucl. Acids Res. 25:3326 3331; and Lobe & Nagy (1998) Bioessays 20:200 208. Each of these references is incorporated herein by reference.

As noted above, transgenic animals and cell lines derived from such animals can find use in certain testing experiments. In this regard, transgenic animals and cell lines capable of expressing wild-type or mutant APAF1 can be exposed to test substances. These test substances can be screened for the ability to alter expression of wild-type APAF1 or alter the expression or function of mutant APAF1.

In a preferred aspect of the invention, compounds that are identified as modulators of APAF1, apoptosome formation, and/or procaspase-9 activation, i.e., drug candidates for treating depression, are tested in animal or cell-based depression models. For example, a drug candidate identified in the screening of the invention methods of the invention is further tested in any of the abovementioned knock-out animal models to evaluate its therapeutic effect. Alternatively, a drug candidate identified in the screening of the invention methods of the invention is further tested in an animal depression model such as the forced swim test, the tail suspension test, learned helplessness test, chronic mild test stress, social stress test, early life stress test, olfactory bulbectomy test, fear conditioning test, anxiety based tests, reward based-tests, and cognition tests. See, e.g., Willner, Adv. Biochem. Psychopharmacol. 49:19 41 (1995); Porsolt, Rev. Neurosci. 11:53 58 (2000); and Nestler et al. Neuron 34:13 25 (2002).

Pharmaceutical Compositions and Routes of Administration

The APAF1 polypeptides, antibodies, peptides and nucleic acids of the present invention can be formulated in pharmaceutical compositions, which are prepared according to conventional pharmaceutical compounding techniques. See, e.g., Remington's Pharmaceutical Sciences, 18th Ed. (1990, Mack Publishing Co., Easton, Pa.). The pharmaceutical compositions of the invention comprise a depression therapeutically effective amount of therapeutic compound. The methods of treating depression comprise administering to an individual in need of treatment a therapeutically effective amount of a pharmaceutical ingredient according to the invention. The composition can contain the active agent or pharmaceutically acceptable salts of the active agent. These compositions can comprise, in addition to one of the active substances, a pharmaceutically acceptable excipient, carrier, buffer, stabilizer or other materials well known in the art. Such materials should be non-toxic and should not interfere with the efficacy of the active ingredient. The carrier can take a wide variety of forms depending on the form of preparation desired for administration, e.g., intravenous, oral, intrathecal, epineural or parenteral.

For oral administration, the compounds can be formulated into solid or liquid preparations such as capsules, pills, tablets, lozenges, melts, powders, suspensions or emulsions. In preparing the compositions in oral dosage form, any of the usual pharmaceutical media may be employed, such as, for example, water, glycols, oils, alcohols, flavoring agents, preservatives, coloring agents, suspending agents, and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets can be sugar-coated or enteric-coated by standard techniques. The active agent can be encapsulated to make it stable to passage through the gastrointestinal tract while at the same time allowing for passage across the blood brain barrier. See, e.g., WO 96/11698.

For parenteral administration, the compound can be dissolved in a pharmaceutical carrier and administered as either a solution or a suspension. Illustrative of suitable carriers are water, saline, dextrose solutions, fructose solutions, ethanol, or oils of animal, vegetative or synthetic origin. The carrier can also contain other ingredients, for example, preservatives, suspending agents, solubilizing agents, buffers and the like.

When the compounds are being administered intrathecally, they can also be dissolved in cerebrospinal fluid.

The active agent is preferably administered in a therapeutically effective amount. The actual amount administered, and the rate and time-course of administration, will depend on the nature and severity of the condition being treated. Prescription of treatment, e.g. decisions on dosage, timing, etc., is within the responsibility of general practitioners or specialists, and typically takes account of the disorder to be treated, the condition of the individual patient, the site of delivery, the method of administration and other factors known to practitioners. Examples of techniques and protocols can be found in Remington's Pharmaceutical Sciences 18th Ed. (1990, Mack Publishing Co., Easton, Pa.).

Alternatively, targeting therapies can be used to deliver the active agent more specifically to certain types of cell, by the use of targeting systems such as antibodies or cell specific ligands. Targeting can be desirable for a variety of reasons, e.g., if the agent is unacceptably toxic, or if it would otherwise require too high a dosage, or if it would not otherwise be able to enter the target cells.

Instead of administering these agents directly, they can be produced in the target cell, e.g. in a viral vector such as described above or in a cell based delivery system such as described in U.S. Pat. No. 5,550,050 and published PCT application Nos. WO 92/19195, WO 94/25503, WO 95/01203, WO 95/05452, WO 96/02286, WO 96/02646, WO 96/40871, WO 96/40959 and WO 97/12635 (all of which are herein incorporated by reference), designed for implantation in a patient. The vector can be targeted to the specific cells to be treated, or it can contain regulatory elements which are more tissue specific to the target cells. The cell based delivery system is designed to be implanted in a patient's body at the desired target site and contains a coding sequence for the active agent. Alternatively, the agent can be administered in a precursor form for conversion to the active form by an activating agent produced in, or targeted to, the cells to be treated. See for example, EP 425,731A and WO 90/07936.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis, T., et al. (1982) Molecular Cloning: A Laboratory Manual (Cold Spring Harbor Laboratory, Cold Spring Harbor, N.Y.); Sambrook, J., et al. (1989) Molecular Cloning: A Laboratory Manual, 2nd Ed. (Cold Spring Harbor Laboratory, Cold Spring Harbor, N.Y.); Ausubel, F. M., et al. (1992) Current Protocols in Molecular Biology, (J. Wiley and Sons, NY); Glover, D. (1985) DNA Cloning, I and II (Oxford Press); Anand, R. (1992) Techniques for the Analysis of Complex Genomes, (Academic Press); Guthrie, G. and Fink, G. R. (1991) Guide to Yeast Genetics and Molecular Biology (Academic Press); Harlow and Lane (1988) Antibodies: A Laboratory Manual (Cold Spring Harbor Laboratory, Cold Spring Harbor, N.Y.; Jakoby, W. B. and Pastan, I. H. (eds.) (1979) Cell Culture. Methods in Enzymology, Vol. 58 (Academic Press, Inc., Harcourt Brace Jovanovich (NY); Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Hogan et al. (eds) (1994) Manipulating the Mouse Embryo. A Laboratory Manual, $2^{nd}$ Edition, Cold Spring Harbor Laboratory Press, Cold Spring Harbor, N.Y. A general discussion of techniques and materials for human gene mapping, including mapping of human chromosome 1, is provided, e.g., in White and Lalouel (1988) Ann. Rev. Genet. 22:259 279.

EXAMPLES

The present invention is described by reference to the following Examples, which are offered by way of illustration and is not intended to limit the invention in any manner. Standard techniques well known in the art or the techniques specifically described below were utilized.

Example 1

Association of APAF1 and Depression

To investigate whether mutations in APAF1 are responsible for the linkage of depression to the chromosomal region 12q23-q24, we carried the analysis with the following parameters.

The phenotype used to assign affected individuals was males affected with either major depression or bipolar disorder. Females were considered uninformative, however this does not imply that the gene found only causes depression in males. Only that the male model was used to get the LOD score. The implication is that it is likely that the phenotype assignment is simpler in males. The model used in the analysis was an affected only model with a dominant mode of inheritance. The resource used to define this linkage was 84 Utah pedigrees with 1507 individuals, 254 of them are affected males. The highest LOD in the study score is 6.1 at marker D12S1706. The region is 7 cM which is about 6.5 million bases and contains approximately 20 genes. The linkage is observed across multiple ethnic populations suggesting that this gene is a major regulator of depression and bipolar disorder and that it is acting in a critical biochemical pathway.

From fifteen families with good evidence for linkage to this region, two affected males who share the segregating haplotype were mutation screened. Variants which change the encoded amino acid (missense changes), were scrutinized for evidence that the variant changes the function of the gene and that the change results in a higher risk of depression. A gene carrying such variants would be a good candidate for the depression susceptibility gene. Causal variants will segregate into other affected individuals in the family and will be rarer in non-cases than in cases.

Caspases are a highly conserved family of cysteine proteases that cleave their substrates after an aspartate residue. They play fundamental roles in the initiation and execution of apoptosis. The APAF1 gene encodes a WD-repeat containing protein. WD-repeat-containing proteins are those that contain 4 or more copies of the WD-repeat (tryptophan-aspartate repeat), a sequence motif approximately 31 amino acids long, that encodes a structural repeat. Activation of procaspase-9 by the APAF1 gene in the cytochrome c/dATP-dependent pathway requires proteolytic cleavage to generate the mature caspase molecule. It was shown that a truncated APAF1 variant lacking the WD-repeat domain makes APAF1 constitutively active and capable of processing procaspase-9 independent of cytochrome c and dATP. Moreover the truncated protein was unable to release the mature caspase-9 from the complex, raising the possibility that the WD-40 repeats play a role in the release of mature caspase-9.

Five different missense changes were detected in linked families in this gene: Cys->Trp at amino acid 450 (C450W) in family 8546 (nucleotide change c1350g), Gln->Arg at amino acid 465 (Q465R) in family 8428 (nucleotide change a1394g), Glu->Lys at amino acid 777 (E777K) in family 8347.2 (nucleotide change g2329a), Asn->Thr at amino acid 782 (A782T) in family 8288 (nucleotide change a2345c) and Thr->Ala at amino acid 953 (T953A) in family 8828803 (nucleotide change a2857g). Additionally, three other mutations have been identified corresponding to Ser357Leu; Asp479Glu; and Glu625Ala. The respective nucleotide changes are C1070T; C1437G; and A1874C. Each one occurs on a haplotype that segregates into more than one affected individual. Although these same missense changes are observed in control individuals, they are less frequent in controls than in cases. In addition to the linked families we are mutation screening an additional 180 male affected cases. To date one frameshift mutation 1299insT (inserts stop codon at codon 439) in family 8205 and another missense change Leu->Pro at amino acid 415 (L415P) in family 8582 (nucleotide change t1244c), have been seen in this random case set. Neither of these changes have been seen in 177 control samples. The protein encoded by the frameshift mutation is set forth in SEQ ID NO:3.

Example 2

Segregating APAF1 Mutants are Capable of Activating Caspase-9 and Caspase-3 in an Apoptosome Reconstitution Assay In order to test the affect of APAF1 mutants that segregate with major depression an apoptosome assay was utilized. Two methods were utilized to determine if the APAF1 segregating mutants were capable of reconstituting a functional apoptosome. First, procaspase-9 conversion to caspase-9 was assessed by SDS-PAGE analysis and western blot analysis using anti-caspase-9. Second, a caspase activation assay was used to determine if procaspase-9 was converted to caspase-9 by assaying for caspase activity.

Figure 2:
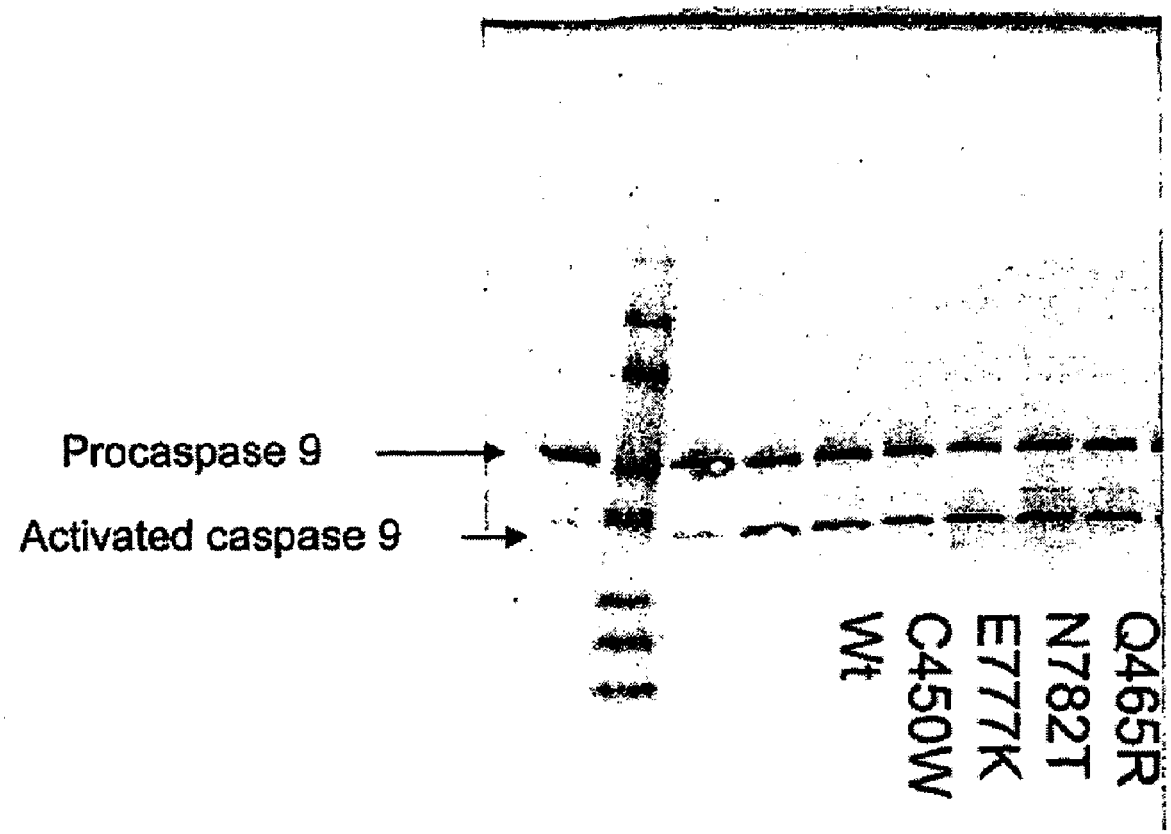
FIG. 2 shows a western blot demonstrating that APAF1 mutants segregating with depression are capable of reconstituting apoptosome activity. See Example 2 for experimental details. Experiment performed at 0.3 mM [caspase], 0.3 or 0.6 mM [Apaf-1], 0.3 mM cytochrome C. Conversion of pro-caspase-9 to caspase-9 is clearly evident as indicated by the bands at the arrows.
Figure 3:
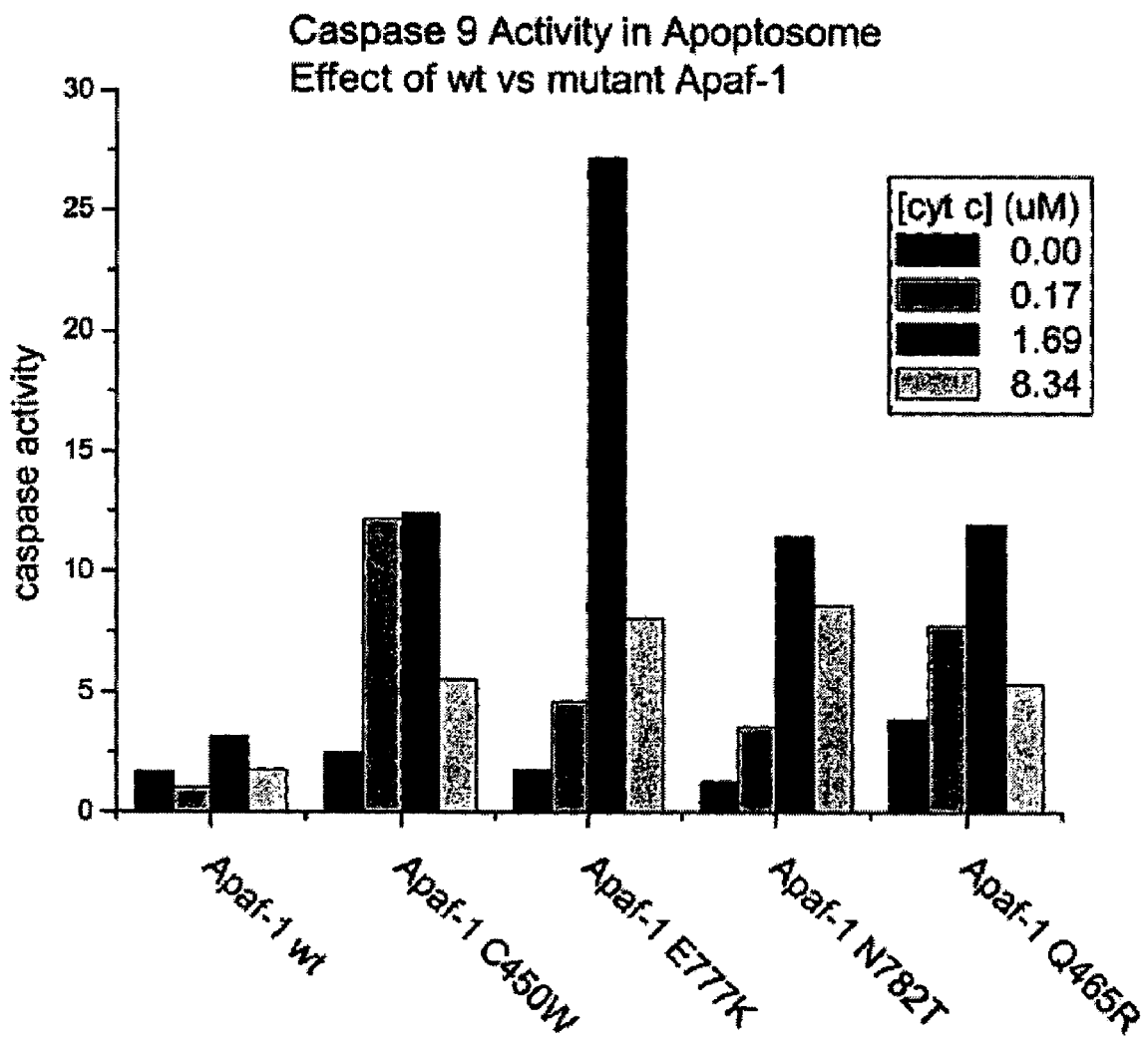
FIG. 3 is a bar graph showing the affect of APAF1 mutants identified as being associated with depression on caspase activation in an in vitro apoptosome assay. See Example 2 for experimental details.

The apoptosome reconstitution assay used in these studies was similar that of Zou et al. J. Biol. Chem., (1999), 274(17): 11549 11556. The assay involved incubating purified cytochrome C, recombinant APAF1 or APAF1 mutants, recombinant procaspase-9, and dATP, in a buffer having 20 mM HEPES, 10 mM KCl, 2.5 mM MgCl2, 1 mM EDTA, 1 mM EGTA, 1 mM DTT, pH 7.5, at 30° C. After a set amount of time, the amount of conversion of procaspase-9 to caspase can be estimated using SDS-PAGE and western blot analysis. These results are shown in FIG. 1 and FIG. 2. Additionally, caspase activation (indicative of procaspase-9 to caspase-9 by the apoptosome) was measured using the caspase substrate Ac-LEHD-pNA (Upstate Biotechnology, NY) in a buffer having 50 mM HEPES, 100 mM NaCl, 0.1% CHAPS, 1 mM EDTA, 10% glycerol, 10 mM DTT, 100 mL total volume, 15 mL apoptosome reconstitution reaction. The reaction progress was monitored at .DELTA.A405 nm. The results of this assay are summarized in FIG. 3.

In summary, the results of the experiments conducted according to this example demonstrate that the APAF1 mutants (particularly C450W, E777K, N782T, and Q465R) discovered as a result of this invention are capable enhancing activation of caspase-9 in a apoptosome activation assay as compared to wild-type APAF1.

Example 3

Primary Apoptosome Screen for Depression Therapeutics

This example relates to identifying compounds that have potential to therapeutically effect depression. The screen of this example can utilize an apoptosome assay. Several configurations of the apoptosome assay can be used to identify depression drug candidates. In one configuration an apoptosome reconstitution assay can be used to identify compounds that inhibit caspase activation. Wild-type APAF1 can be used in the apoptosome assay and compounds that reduce caspase activation as compared to control is identified as a potential depression therapeutic. Alternatively, mutant APAF1 (e.g., those discovered as a result of the invention) can be used in the apoptosome assay. The apoptosome having mutant APAF1 is expected to display increased caspase activation as compared to wild-type APAF1. Upon incubation of apoptosome having mutant APAF1, compounds that reduce caspase activation are considered to be potential depression therapeutics. In another configuration, the apoptosome can be reconstituted in the presence of a compound known to enhance caspase activation by increasing the activity of the apoptosome. Compounds known to activate apoptosis via the apoptosome are known and disclosed in Nguyen et al. PNAS 100:7533 7538 (2003) and Jiang et al. Science 299:223 226 (2003). One such compound is α-(trichloromethyl)-4-pyridineethanol. The ability of test compounds to reverse the enhancement of activation is indicative of a drug candidate for treating depression.

Again, any method can be used to determine the affect of test compounds for their ability to reconstitute a functional apoptosome. In one method, activity can be monitored by procaspase-9 conversion to caspase-9 can assessed by SDS-PAGE analysis and western blot analysis using anti-caspase-9. In another method, a caspase activation assay can be used to determine if procaspase-9 is converted to caspase-9 by assaying for caspase-3 activity.

The apoptosome reconstitution assay that can be used in these studies is similar that of Zou et al. J. Biol. Chem., (1999), 274(17):11549 11556. The assay involves incubating purified cytochrome C, recombinant APAF1 or APAF1 mutants, recombinant procaspase-9, and dATP, in a buffer having 20 mM HEPES, 10 mM KCl, 2.5 mM MgCl2, 1 mM EDTA, 1 mM EGTA, 1 mM DTT, pH 7.5 at 30° C. After a set amount of time, the amount of conversion of procaspase-9 to caspase can be estimated using SDS-PAGE and western blot analysis. Additionally, caspase activation (indicative of procaspase-9 to caspase-9 by the apoptosome) can be measured using the caspase substrate Ac-LEHD-pNA (Upstate Biotechnology, NY) in a buffer having 50 mM HEPES, 100 mM NaCl, 0.1% CHAPS, 1 mM EDTA, 10% glycerol, 10 mM DTT, 100 mL total volume, 15 mL apoptosome reconstitution reaction. The reaction progress can be monitored at .DELTA.A405 nm.

In summary, compounds capable enhancing activation of the mutant APAF1 apoptosomes in the apoptosome activation

Example 4

Screen of APAF1 Oligimerization Disrupters

Drug candidate for treating depression can be identified by screening for molecules that disrupt the oligimerization of APAF1. According to this example, a truncated version of APAF1, which is constitutively active, can be used to identify potential depression therapeutics. The truncated version of APAF1 can be any APAF1 as long as it is constitutively active. Truncated APAF1 is disclosed in Srinivasula et al. Mol. Cell. 1 949 957 (1998), Hu et al. EMBO J. 18, 3586 3595 (1999), or according to SEQ ID NO:3 as disclosed herein. The truncated APAF1 can also have any of the mutations disclosed herein.

Assay solution having truncated APAF1 and procaspase-9 is incubated in the presence and absence of test compound. Test compounds which reduce the level of procaspase-9 (or procaspase-3) activation as compared to an identical assay without the test compound is considered a potential depression therapeutic. Procaspase-9 and/or procaspase-3 activation can be determined according to the examples described herein. The skilled artisan is capable of determining pro-caspase-9 and/or procaspase-3 activation.

Example 5

Secondary Screen of Apoptosome Disrupters in Animal Depression Models

Test compounds identified in the screens of the invention as potential depression therapeutics are desirably further tested in an animal depression model. The potential depression therapeutics can be tested in transgenic animals being homozygous or heterozygous for a mutant APAF1. For example a transgenic animal being homozygous or heterozygous for a mutant APAF1 well display a certain phenotype, animal treated with potential depression therapeutics that are capable of modifying depression are expected to modify that phenotype. Thus, a group of untreated animals can be compared to a group of animal treated with the potential depression therapeutic. The treated group is expected to display an improved phenotype. Any phenotypic measurement known to the skilled artisan can be used to assess the treatment.

Alternatively, the test compounds identified in the screens of the invention as potential depression therapeutics are desirably tested in an art-accepted animal depression model such as those in Willner, Adv. Biochem. Psychopharmacol. 49:19 41 (1995); Porsolt, Rev. Neurosci. 11:53 58 (2000); and Nestler et al. Neuron 34:13 25 (2002). These tests can include the forced swim test, the tail suspension test, learned helplessness test, chronic mild test stress, social stress test, early life stress test, olfactory bulbectomy test, fear conditioning test, anxiety based tests, reward based-tests, and cognition tests. A potential depression therapeutic identified in the screens of the invention has anti-depression activity if it increases the struggle time in the forced swim test, increases struggle time in the tail suspension test, decrease escape time and latency in the learned helplessness test, increased sexual behavior or sucrose preference in the chronic mild stress test, decrease behavioral abnormalities in the social stress test, reverse behavioral problems in the early life stress test, reverses behavioral abnormalities in the olfactory bulbectomy test, decreases fear-like response when exposed to previously neutral cues that have been associated with adverse stimuli, increase the degree to which an animal explores a particular environment in an anxiety based test, and so on.

While the invention has been disclosed in this patent application by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

The publications and other materials used herein to illuminate the background of the invention, and in particular, cases to provide additional details respecting the practice, are incorporated herein by reference.

What is claimed is:

1. A method for detecting susceptibility to depression in an individual comprising:
   a) drawing a sample of DNA from any tissue in the individual; and
   b) using a diagnostic technique to detect a genetic alteration in the wild-type APAF1 allele (SEQ ID NO: 1), said genetic alteration comprising at least one nucleic acid alteration selected from the group consisting of C1350G, A1394G, G2329A, A2345C, A2857G, insertion of a T after nucleotide position 1299, T1244C, C1070T, C1437G, and A1874C,
   wherein detection of said genetic alteration indicates that said individual is susceptible to depression.

2. The method according to claim 1, wherein the diagnostic technique is selected from the group consisting of fluorescent in situ hybridization (FISH), direct DNA sequencing, pulsed-field gel electrophoresis (PFGE) analysis, Southern blot analysis, single stranded conformation analysis (SSCA), denaturing gradient gel electrophoresis (DGGE), RNase protection assay, allele-specific oligonucleotide (ASO), dot blot analysis, allele specific polymerase chain reaction (PCR), DNA microchip technology, and PCR-SSCA.

3. The method according to claim 1, wherein the diagnostic technique includes molecular cloning of the APAF1 allele(s) and sequencing the allele(s).

4. The method according to claim 1, wherein the diagnostic technique includes amplifying the gene sequences directly from a genomic DNA preparation.

5. The method according to claim 1, wherein the diagnostic technique includes sequencing mutant alleles to identify the specific mutation for each allele.

* * * * *

SEQUENCE LISTING

```
<160> NUMBER OF SEQ ID NOS: 3

<210> SEQ ID NO 1
<211> LENGTH: 3747
<212> TYPE: DNA
<213> ORGANISM: Homo Sapiens

<400> SEQUENCE: 1
atggatgcaa aagctcgaaa ttgtttgctt caacatagag aagctctgga aaaggacatc      60
aagacatcct acatcatgga tcacatgatt agtgatggat ttttaacaat atcagaagag     120
gaaaaagtaa gaaatgagcc cactcaacag caaagagcag ctatgctgat taaaatgata     180
cttaaaaaag ataatgattc ctacgtatca ttctacaatg ctctactaca tgaaggatat     240
aaagatcttg ctgcccttct ccatgatggc attcctgttg tctcttcttc cagtggtaaa     300
gattcagtta gtggaataac ttcgtatgta aggacagtcc tgtgtgaagg tggagtacca     360
cagaggccag ttgtttttgt cacaaggaag aagctggtga atgcaattca gcagaagctc     420
tccaaattga aaggtgaacc aggatgggtc accatacatg gaatggcagg ctgtgggaag     480
```

```
tctgtattag ctgcagaagc tgttagagat cattcccttt tagaaggttg tttcccaggg    540
ggagtgcatt gggtttcagt tgggaaacaa gacaaatctg ggcttctgat gaaactgcag    600
aatctttgca cacggttgga tcaggatgag agttttttccc agaggcttcc acttaatatt    660
gaagaggcta aagaccgtct ccgcattctg atgcttcgca aacacccaag gtctctcttg    720
atcttggatg atgtttggga ctcttgggtg ttgaaagctt ttgacagtca gtgtcagatt    780
cttcttacaa ccagagacaa gagtgttaca gattcagtaa tgggtcctaa atatgtagtc    840
cctgtggaga gttccttagg aaaggaaaaa ggacttgaaa ttttatccct ttttgttaat    900
atgaagaagg cagatttgcc agaacaagct catagtatta taaaagaatg taaaggctct    960 cccccttgtag tatctttaat tggtgcactt ttacgtgatt ttcccaatcg ctgggagtac   1020
tacctcaaac agcttcagaa taagcagttt aagagaataa ggaaatcttc gtcttatgat   1080
tatgaggctc tagatgaagc catgtctata agtgttgaaa tgctcagaga agacatcaaa   1140
gattattaca cagatctttc catccttcag aaggacgtta aggtgcctac aaaggtgtta   1200
tgtattctct gggacatgga aactgaagaa gttgaagaca tactgcagga gtttgtaaat   1260
aagtctcttt tattctgtga tcggaatgga aagtcgtttc gttattattt acatgatctt   1320
caagtagatt ttcttacaga gaagaattgc agccagcttc aggatctaca taagaagata   1380
atcactcagt ttcagagata tcaccagccg catactcttt caccagatca ggaagactgt   1440
atgtattggt acaactttct ggcctatcac atggccagtg ccaagatgca caggaacctt   1500
tgtgctttaa tgttttccct ggattggatt aaagcaaaaa cagaacttgt aggccctgct   1560
catctgattc atgaatttgt ggaatacaga catatactag atgaaaagga ttgtgcagtc   1620
agtgagaatt ttcaggagtt tttatcttta aatggacacc ttcttggacg acagccattt   1680
cctaatattg tacaactggg tctctgtgag ccggaaactt cagaagttta tcagcaagct   1740
aagctgcagg ccaagcagga ggtcgataat ggaatgcttt acctggaatg gataaacaaa   1800
aaaaacatca cgaatctttc ccgcttagtt gtccgcccccc acacagatgc tgtttaccat   1860
gcctgctttt ctgaggatgg tcagagaata gcttcttgtg gagctgataa aaccttacag   1920
gtgttcaaag ctgaaacagg agagaaactt ctagaaatca aggctcatga ggatgaagtg   1980
ctttgttgtg cattctctac agatgacaga tttatagcaa cctgctcagt ggataaaaaa   2040
gtgaagattt ggaattctat gactggggaa ctagtacaca cctatgatga gcactcagag   2100
caagtcaatt gctgccattt caccaacagt agtcatcatc ttctcttagc cactgggtca   2160
agtgactgct tcctcaaact ttgggatttg aatcaaaaag aatgtcgaaa taccatgttt   2220
ggtcatacaa attcagtcaa tcactgcaga ttttcaccag atgataagct tttggctagt   2280
tgttcagctg atggaacctt aaagctttgg gatgcgacat cagcaaatga gaggaaaagc   2340
attaatgtga aacagttctt cctaaatttg gaggaccctc aagaggatat ggaagtgata   2400
gtgaagtgtt gttcgtggtc tgctgatggt gcaaggataa tggtggcagc aaaaaataaa   2460
atctttcttt ttgacattca tactagtggc ctattgggag aaatccacac gggccatcac   2520
agcaccatcc agtactgtga cttctcccca caaaaccatt tggcagtggt tgctttgtcc   2580
cagtactgtg tagagttgtg aatacagac tcacgttcaa aggtggctga ttgcagagga   2640
catttaagtt gggttcatgg tgtgatgttt tctcctgatg gatcatcatt tttgacatct   2700
tctgatgacc agacaatcag gctctgggag acaaagaaag tatgtaagaa ctctgctgta   2760
atgttaaagc aagaagtaga tgttgtgttt caagaaaatg aagtgatggt ccttgcagtt   2820
```

-continued

```
gaccatataa gacgtctgca actcattaat ggaagaacag gtcagattga ttatctgact    2880
gaagctcaag ttagctgctg ttgcttaagt ccacatcttc agtacattgc atttggagat    2940
gaaaatggag ccattgagat tttagaactt gtaaacaata gaatcttcca gtccaggttt    3000
cagcacaaga aaactgtatg gcacatccag ttcacagccg atgagaagac tcttatttca    3060
agttctgatg atgctgaaat tcaggtatgg aattggcaat tggacaaatg tatcttttcta   3120 cgaggccatc aggaaacagt gaaagacttt agactcttga aaaattcaag actgctttct    3180
tggtcatttg atggaacagt gaaggtatgg aatattatta ctggaaataa agaaaaagac    3240
tttgtctgtc accagggtac agtactttct tgtgacattt ctcacgatgc taccaagttt    3300
tcatctacct ctgctgacaa gactgcaaag atctggagtt ttgatctcct tttgccactt    3360
catgaattga ggggccacaa cggctgtgtg cgctgctctg ccttctctgt ggacagtacc    3420
ctgctggcaa cgggagatga caatggagaa atcaggatat ggaatgtctc aaacggtgag    3480
cttcttcatt tgtgtgctcc gctttcagaa gaaggagctg ctacccatgg aggctgggtg    3540
actgaccttt gctttctcc agatggcaaa atgcttatct ctgctggagg atatattaag    3600
tggtggaacg ttgtcactgg ggaatcctca cagaccttct acacaaatgg aaccaatctt    3660
aagaaaatac acgtgtcccc tgacttcaaa acatatgtga ctgtggataa tcttggtatt    3720
ttatatattt tacagacttt agaataa                                         3747
```

<210> SEQ ID NO 2
<211> LENGTH: 1248
<212> TYPE: PRT
<213> ORGANISM: Homo Sapiens

<400> SEQUENCE: 2

```
Met Asp Ala Lys Ala Arg Asn Cys Leu Leu Gln His Arg Glu Ala Leu
1               5                   10                  15

Glu Lys Asp Ile Lys Thr Ser Tyr Ile Met Asp His Met Ile Ser Asp
            20                  25                  30

Gly Phe Leu Thr Ile Ser Glu Glu Lys Val Arg Asn Glu Pro Thr
        35                  40                  45

Gln Gln Gln Arg Ala Ala Met Leu Ile Lys Met Ile Leu Lys Lys Asp
    50                  55                  60

Asn Asp Ser Tyr Val Ser Phe Tyr Asn Ala Leu His Glu Gly Tyr
65                  70                  75                  80

Lys Asp Leu Ala Ala Leu Leu His Asp Gly Ile Pro Val Val Ser Ser
                85                  90                  95

Ser Ser Gly Lys Asp Ser Val Ser Gly Ile Thr Ser Tyr Val Arg Thr
            100                 105                 110

Val Leu Cys Glu Gly Gly Val Pro Gln Arg Pro Val Val Phe Val Thr
        115                 120                 125

Arg Lys Lys Leu Val Asn Ala Ile Gln Gln Lys Leu Ser Lys Leu Lys
    130                 135                 140

Gly Glu Pro Gly Trp Val Thr Ile His Gly Met Ala Gly Cys Gly Lys
145                 150                 155                 160

Ser Val Leu Ala Ala Glu Ala Val Arg Asp His Ser Leu Leu Glu Gly
                165                 170                 175

Cys Phe Pro Gly Gly Val His Trp Val Ser Val Gly Lys Gln Asp Lys
            180                 185                 190

Ser Gly Leu Leu Met Lys Leu Gln Asn Leu Cys Thr Arg Leu Asp Gln
        195                 200                 205
```

-continued

```
Asp Glu Ser Phe Ser Gln Arg Leu Pro Leu Asn Ile Glu Glu Ala Lys
    210                 215                 220

Asp Arg Leu Arg Ile Leu Met Leu Arg Lys His Pro Arg Ser Leu Leu
225                 230                 235                 240

Ile Leu Asp Asp Val Trp Asp Ser Trp Val Leu Lys Ala Phe Asp Ser
                245                 250                 255

Gln Cys Gln Ile Leu Leu Thr Thr Arg Asp Lys Ser Val Thr Asp Ser
            260                 265                 270

Val Met Gly Pro Lys Tyr Val Pro Val Glu Ser Ser Leu Gly Lys
        275                 280                 285

Glu Lys Gly Leu Glu Ile Leu Ser Leu Phe Val Asn Met Lys Lys Ala
    290                 295                 300

Asp Leu Pro Glu Gln Ala His Ser Ile Ile Lys Glu Cys Lys Gly Ser
305                 310                 315                 320

Pro Leu Val Val Ser Leu Ile Gly Ala Leu Leu Arg Asp Phe Pro Asn
                325                 330                 335

Arg Trp Glu Tyr Tyr Leu Lys Gln Leu Gln Asn Lys Gln Phe Lys Arg
            340                 345                 350

Ile Arg Lys Ser Ser Tyr Asp Tyr Glu Ala Leu Asp Glu Ala Met
            355                 360                 365

Ser Ile Ser Val Glu Met Leu Arg Glu Asp Ile Lys Asp Tyr Tyr Thr
370                 375                 380

Asp Leu Ser Ile Leu Gln Lys Asp Val Lys Val Pro Thr Lys Val Leu
385                 390                 395                 400

Cys Ile Leu Trp Asp Met Glu Thr Glu Glu Val Glu Asp Ile Leu Gln
                405                 410                 415

Glu Phe Val Asn Lys Ser Leu Leu Phe Cys Asp Arg Asn Gly Lys Ser
            420                 425                 430

Phe Arg Tyr Tyr Leu His Asp Leu Gln Val Asp Phe Leu Thr Glu Lys
        435                 440                 445

Asn Cys Ser Gln Leu Gln Asp Leu His Lys Lys Ile Ile Thr Gln Phe
450                 455                 460

Gln Arg Tyr His Gln Pro His Thr Leu Ser Pro Asp Gln Glu Asp Cys
465                 470                 475                 480

Met Tyr Trp Tyr Asn Phe Leu Ala Tyr His Met Ala Ser Ala Lys Met
                485                 490                 495

His Lys Glu Leu Cys Ala Leu Met Phe Ser Leu Asp Trp Ile Lys Ala
            500                 505                 510

Lys Thr Glu Leu Val Gly Pro Ala His Leu Ile His Glu Phe Val Glu
        515                 520                 525

Tyr Arg His Ile Leu Asp Glu Lys Asp Cys Ala Val Ser Glu Asn Phe
    530                 535                 540

Gln Glu Phe Leu Ser Leu Asn Gly His Leu Leu Gly Arg Gln Pro Phe
545                 550                 555                 560

Pro Asn Ile Val Gln Leu Gly Leu Cys Glu Pro Glu Thr Ser Glu Val
                565                 570                 575

Tyr Gln Gln Ala Lys Leu Gln Ala Lys Glu Val Asp Asn Gly Met
            580                 585                 590

Leu Tyr Leu Glu Trp Ile Asn Lys Lys Asn Ile Thr Asn Leu Ser Arg
        595                 600                 605

Leu Val Val Arg Pro His Thr Asp Ala Val Tyr His Ala Cys Phe Ser
    610                 615                 620

Glu Asp Gly Gln Arg Ile Ala Ser Cys Gly Ala Asp Lys Thr Leu Gln
```

-continued

```
            625                 630                 635                 640
Val Phe Lys Ala Glu Thr Gly Glu Lys Leu Leu Glu Ile Lys Ala His
                    645                 650                 655
Glu Asp Glu Val Leu Cys Cys Ala Phe Ser Thr Asp Arg Phe Ile
            660                 665                 670
Ala Thr Cys Ser Val Asp Lys Val Lys Ile Trp Asn Ser Met Thr
            675                 680                 685
Gly Glu Leu Val His Thr Tyr Asp Glu His Ser Glu Gln Val Asn Cys
            690                 695                 700
Cys His Phe Thr Asn Ser Ser His His Leu Leu Leu Ala Thr Gly Ser
705                 710                 715                 720
Ser Asp Cys Phe Leu Lys Leu Trp Asp Leu Asn Gln Lys Glu Cys Arg
                    725                 730                 735
Asn Thr Met Phe Gly His Thr Asn Ser Val Asn His Cys Arg Phe Ser
            740                 745                 750
Pro Asp Asp Lys Leu Leu Ala Ser Cys Ser Ala Asp Gly Thr Leu Lys
            755                 760                 765
Leu Trp Asp Ala Thr Ser Ala Asn Glu Arg Lys Ser Ile Asn Val Lys
770                 775                 780
Gln Phe Phe Leu Asn Leu Glu Asp Pro Gln Glu Asp Met Glu Val Ile
785                 790                 795                 800
Val Lys Cys Cys Ser Trp Ser Ala Asp Gly Ala Arg Ile Met Val Ala
                    805                 810                 815
Ala Lys Asn Lys Ile Phe Leu Phe Asp Ile His Thr Ser Gly Leu Leu
            820                 825                 830
Gly Glu Ile His Thr Gly His His Ser Thr Ile Gln Tyr Cys Asp Phe
            835                 840                 845
Ser Pro Gln Asn His Leu Ala Val Val Ala Leu Ser Gln Tyr Cys Val
            850                 855                 860
Glu Leu Trp Asn Thr Asp Ser Arg Ser Lys Val Ala Asp Cys Arg Gly
865                 870                 875                 880
His Leu Ser Trp Val His Gly Val Met Phe Ser Pro Asp Gly Ser Ser
                    885                 890                 895
Phe Leu Thr Ser Ser Asp Asp Gln Thr Ile Arg Leu Trp Glu Thr Lys
            900                 905                 910
Lys Val Cys Lys Asn Ser Ala Val Met Leu Lys Gln Glu Val Asp Val
            915                 920                 925
Val Phe Gln Glu Asn Glu Val Met Val Leu Ala Val Asp His Ile Arg
            930                 935                 940
Arg Leu Gln Leu Ile Asn Gly Arg Thr Gly Gln Ile Asp Tyr Leu Thr
945                 950                 955                 960
Glu Ala Gln Val Ser Cys Cys Leu Ser Pro His Leu Gln Tyr Ile
            965                 970                 975
Ala Phe Gly Asp Glu Asn Gly Ala Ile Glu Ile Leu Glu Leu Val Asn
            980                 985                 990
Asn Arg Ile Phe Gln Ser Arg Phe Gln His Lys Lys Thr Val Trp His
            995                 1000                1005
Ile Gln Phe Thr Ala Asp Glu Lys Thr Leu Ile Ser Ser Ser Asp Asp
            1010                1015                1020
Ala Glu Ile Gln Val Trp Asn Trp Gln Leu Asp Lys Cys Ile Phe Leu
1025                1030                1035                1040
Arg Gly His Gln Glu Thr Val Lys Asp Phe Arg Leu Leu Lys Asn Ser
                    1045                1050                1055
```

-continued

```
Arg Leu Leu Ser Trp Ser Phe Asp Gly Thr Val Lys Val Trp Asn Ile
            1060                1065                1070

Ile Thr Gly Asn Lys Glu Lys Asp Phe Val Cys His Gln Gly Thr Val
        1075                1080                1085

Leu Ser Cys Asp Ile Ser His Asp Ala Thr Lys Phe Ser Ser Thr Ser
    1090                1095                1100

Ala Asp Lys Thr Ala Lys Ile Trp Ser Phe Asp Leu Leu Pro Leu
1105                1110                1115                1120

His Glu Leu Arg Gly His Asn Gly Cys Val Arg Cys Ser Ala Phe Ser
                1125                1130                1135

Val Asp Ser Thr Leu Leu Ala Thr Gly Asp Asp Asn Gly Glu Ile Arg
            1140                1145                1150

Ile Trp Asn Val Ser Asn Gly Glu Leu Leu His Leu Cys Ala Pro Leu
        1155                1160                1165

Ser Glu Glu Gly Ala Ala Thr His Gly Gly Trp Val Thr Asp Leu Cys
    1170                1175                1180

Phe Ser Pro Asp Gly Lys Met Leu Ile Ser Ala Gly Gly Tyr Ile Lys
1185                1190                1195                1200

Trp Trp Asn Val Val Thr Gly Glu Ser Ser Gln Thr Phe Tyr Thr Asn
                1205                1210                1215

Gly Thr Asn Leu Lys Lys Ile His Val Ser Pro Asp Phe Lys Thr Tyr
            1220                1225                1230

Val Thr Val Asp Asn Leu Gly Ile Leu Tyr Ile Leu Gln Thr Leu Glu
        1235                1240                1245

<210> SEQ ID NO 3
<211> LENGTH: 438
<212> TYPE: PRT
<213> ORGANISM: Homo Sapiens

<400> SEQUENCE: 3

Met Asp Ala Lys Ala Arg Asn Cys Leu Leu Gln His Arg Glu Ala Leu
1               5                   10                  15

Glu Lys Asp Ile Lys Thr Ser Tyr Ile Met Asp His Met Ile Ser Asp
            20                  25                  30

Gly Phe Leu Thr Ile Ser Glu Glu Lys Val Arg Asn Glu Pro Thr
        35                  40                  45

Gln Gln Gln Arg Ala Ala Met Leu Ile Lys Met Ile Leu Lys Lys Asp
    50                  55                  60

Asn Asp Ser Tyr Val Ser Phe Tyr Asn Ala Leu Leu His Glu Gly Tyr
65                  70                  75                  80

Lys Asp Leu Ala Ala Leu Leu His Asp Gly Ile Pro Val Val Ser Ser
                85                  90                  95

Ser Ser Gly Lys Asp Ser Val Ser Gly Ile Thr Ser Tyr Val Arg Thr
            100                 105                 110

Val Leu Cys Glu Gly Gly Val Pro Gln Arg Pro Val Val Phe Val Thr
        115                 120                 125

Arg Lys Lys Leu Val Asn Ala Ile Gln Gln Lys Leu Ser Lys Leu Lys
    130                 135                 140

Gly Glu Pro Gly Trp Val Thr Ile His Gly Met Ala Gly Cys Gly Lys
145                 150                 155                 160

Ser Val Leu Ala Ala Glu Ala Val Arg Asp His Ser Leu Leu Glu Gly
                165                 170                 175

Cys Phe Pro Gly Gly Val His Trp Val Ser Val Gly Lys Gln Asp Lys
```

-continued

```
                    180                 185                 190
Ser Gly Leu Leu Met Lys Leu Gln Asn Leu Cys Thr Arg Leu Asp Gln
        195                 200                 205

Asp Glu Ser Phe Ser Gln Arg Leu Pro Leu Asn Ile Glu Glu Ala Lys
        210                 215                 220

Asp Arg Leu Arg Ile Leu Met Leu Arg Lys His Pro Arg Ser Leu Leu
225                 230                 235                 240

Ile Leu Asp Asp Val Trp Asp Ser Trp Val Leu Lys Ala Phe Asp Ser
                245                 250                 255

Gln Cys Gln Ile Leu Leu Thr Thr Arg Asp Lys Ser Val Thr Asp Ser
                260                 265                 270

Val Met Gly Pro Lys Tyr Val Val Pro Val Glu Ser Ser Leu Gly Lys
        275                 280                 285

Glu Lys Gly Leu Glu Ile Leu Ser Leu Phe Val Asn Met Lys Lys Ala
        290                 295                 300

Asp Leu Pro Glu Gln Ala His Ser Ile Ile Lys Glu Cys Lys Gly Ser
305                 310                 315                 320

Pro Leu Val Val Ser Leu Ile Gly Ala Leu Leu Arg Asp Phe Pro Asn
                325                 330                 335

Arg Trp Glu Tyr Tyr Leu Lys Gln Leu Gln Asn Lys Gln Phe Lys Arg
                340                 345                 350

Ile Arg Lys Ser Ser Ser Tyr Asp Tyr Glu Ala Leu Asp Glu Ala Met
        355                 360                 365

Ser Ile Ser Val Glu Met Leu Arg Glu Asp Ile Lys Asp Tyr Tyr Thr
        370                 375                 380

Asp Leu Ser Ile Leu Gln Lys Asp Val Lys Val Pro Thr Lys Val Leu
385                 390                 395                 400

Cys Ile Leu Trp Asp Met Glu Thr Glu Glu Val Glu Asp Ile Leu Gln
                405                 410                 415

Glu Phe Val Asn Lys Ser Leu Leu Phe Cys Asp Arg Asn Gly Lys Ser
                420                 425                 430

Phe Ser Leu Leu Phe Thr
                435
```